US012604823B2

(12) United States Patent
Tanaka et al.

(10) Patent No.: US 12,604,823 B2
(45) Date of Patent: Apr. 21, 2026

(54) *SPINACIA* PLANT WITH LOW OXALIC ACID CONTENT

(71) Applicant: TOHOKU SEED CO., LTD., Utsunomiya (JP)

(72) Inventors: Atsushi Tanaka, Tochigi (JP); Kei Ogasawara, Tochigi (JP); Kei Koyasaki, Tochigi (JP); Norifumi Tanaka, Tochigi (JP); Satoshi Niikura, Tochigi (JP); Fumio Azuhata, Tochigi (JP)

(73) Assignee: TOHOKU SEED CO., LTD., Utsunomiya (JP)

( * ) Notice: Subject to any disclaimer, the term of this patent is extended or adjusted under 35 U.S.C. 154(b) by 462 days.

(21) Appl. No.: 17/760,270

(22) PCT Filed: Mar. 31, 2020

(86) PCT No.: PCT/JP2020/014904
§ 371 (c)(1),
(2) Date: Aug. 5, 2022

(87) PCT Pub. No.: WO2021/199326
PCT Pub. Date: Oct. 7, 2021

(65) Prior Publication Data
US 2023/0073688 A1 Mar. 9, 2023

(51) Int. Cl.
A01H 5/02 (2018.01)
A01H 6/02 (2018.01)

(52) U.S. Cl.
CPC ................. *A01H 6/02* (2018.05); *A01H 5/02* (2013.01)

(58) Field of Classification Search
None
See application file for complete search history.

(56) References Cited

U.S. PATENT DOCUMENTS 8,563,807 B2 * 10/2013 Dijkstra ................. A01H 6/028
800/278

FOREIGN PATENT DOCUMENTS

JP 2014-150763 A 8/2014

OTHER PUBLICATIONS

Mou, Beiquan. HortScience (2008), 43(6):1690-1693.*
(Continued)

*Primary Examiner* — Medina A Ibrahim
(74) *Attorney, Agent, or Firm* — Oblon, McClelland, Maier & Neustadt, L.L.P.

(57) ABSTRACT

A *spinacia* plant with a low oxalic acid content, in particular a low oxalic acid content that is stable and unaffected by environmental conditions. A method for producing the same, a screening method, and a screening kit. A *spinacia* plant with a low oxalic acid content having at least one low oxalic acid locus located in a chromosome 4 region; a method for producing the *spinacia* plant having the low oxalic acid content through cross breeding the *spinacia* plant having the low oxalic acid content with another *spinacia* plant. A method for screening *spinacia* plants with low oxalic acid contents by selecting the *spinacia* plant having at least one low oxalic acid locus located in the chromosome 4 region. A kit for screening *spinacia* plants with low oxalic acid contents having a primer or a probe that is specifically bound to the low oxalic acid locus.

12 Claims, No Drawings
Specification includes a Sequence Listing.

(56)               References Cited

OTHER PUBLICATIONS

Murakami et al. J. Japan. Soc. Hort. Sci (2009)78(2):180-184.*
Okutani et al. HortScience (1994), 29(9):1019-1021.*
Grobkinsky et al. Journal of Experimental Botany (2015), 66(18):5429-5440.*
Huan et al. Plant Physiology (2011) 155:645-655.*
International Search Report issued Jun. 23, 2020, in PCT/JP2020/014904 filed Mar. 31, 2020, 2 pages.
Shi, A. et al. "Association analysis for oxalate concentration in spinach", Euphytica, 2016, vol. 212, pp. 17-28.
Cai, X. et al. "Expression Analysis of Oxalate Metabolic Pathway Genes Reveals Oxalate Regulation Patterns in Spinach", Molecules, 2018, vol. 23, 15 pages.
Xu, C. et al. "Draft genome of spinach and transcriptome diversity of 120 Spinacia accessions", Nature Communications, 2017, 10 pages.
Kagawa, A. "Cultivation physiology of high quality spinach", Ishizue-publishing Corp., 1997, (with translation), pp. 74-84.
Libert, B. et al. "Oxalate in Crop Plants", J.Agric. Food Chem. vol. 35, 1987, pp. 926-938.
The Japanese Urological Association, The Japanese Society of Endourology, The Japanese Society of Urolithiasis Research "Guide-lines for the diagnosis of urolithiasis 2013 edition", Kanehara & Co., Ltd., 2013, 4 pages, (with translation), https://minds.jcqhc.or.jp/n/med/4/med0022/G0000634/0021.
Taylor, E.N. et al. "Oxalate Intake and the Risk for Nephrolithiasis", J Am Soc Nephrol, vol. 18, 2007, pp. 2198-2204.
Kaminishi A. et al. "Seasonal Change of Nitrate and Oxalate Concentration in Relation to the Growth Rate of Spinach Cultivars", HortScience, vol. 41, No. 7, 2006, pp. 1589-1595.
Kawazu, Y. et al. "Varietal and seasonal differences in oxalate content of spinach", Scientia Horticarturae vol. 97, 2002, pp. 203-210.
Elia, A. et al. "Nitrogen Nutrition, Yield and Quality of Spinach", J Sci Food Agric, vol. 76, 1998, pp. 341-346.
Solberg, S.O. et al. "Nitrate and oxalate in germplasm collections of spinach and other leafy vegetables", Emirates Journal of Food and Agriculture, vol. 27, No. 9, 2015, pp. 698-705.
Mitsui, K. "Spinach cultivating people, Journey for Japanese spin-ach, from 17 cultivation sites", published by Seibundo-shinkosha, 2006, (with translation), 9 pages.
Murakami, K. et al. "Low-oxalate Spinach Mutant Induced by Chemical Mutagenesis", J.Japan. Soc. Hort. Sci. Vol. 78, No. 2, 2009, pp. 180-184.

* cited by examiner

SEQUENCE LISTING

<160> NUMBER OF SEQ ID NOS: 22

<210> SEQ ID NO 1
<211> LENGTH: 101
<212> TYPE: DNA
<213> ORGANISM: Spinacia oleracea

<400> SEQUENCE: 1
cacgaaataa gtcaaactta tttatttttc tttttagtag aaattatctt ttctaattaa       60
ctaataatgt atataaaaat tatccataaa aaattacgga g                          101

<210> SEQ ID NO 2
<211> LENGTH: 101
<212> TYPE: DNA

<213> ORGANISM: Spinacia oleracea

<400> SEQUENCE: 2
aagttttgat tgttcgacat atttttaaa gcgtaaagaa tttaatgaaa tagatgtatt          60
atgtgttaga tatcgaagtt gtatatgacc aagaagaaaa t                           101

<210> SEQ ID NO 3
<211> LENGTH: 269
<212> TYPE: DNA
<213> ORGANISM: Spinacia oleracea

<400> SEQUENCE: 3
gttaaggacc tcttgctcct taatcaaggt cccgggttcg agccttggaa atgaaaaaaa          60
tctcaactgg gaggatgctg cccatcgaaa tacccatgca aactcccgcg gaagattagt         120
ccactcgccg aagggcgtgg gaactcctcg tagtagaaca aaaaaaaaca atttgaagaa         180
atactgacta taaaaatttg ctgctattaa taaaatgtcc aataagtcgg taactatcct         240
tcttactccc tccttaaatt tggattggg                                          269

<210> SEQ ID NO 4
<211> LENGTH: 101
<212> TYPE: DNA
<213> ORGANISM: Spinacia oleracea

<400> SEQUENCE: 4
gtctcccttg aagagaacat agccaacctc gacgaggccg cgaccgaggg atccaatagg          60
aggagtgggt tggttgttgt ctcagctaac ttctgttttt g                           101

<210> SEQ ID NO 5
<211> LENGTH: 101
<212> TYPE: DNA
<213> ORGANISM: Spinacia oleracea

<400> SEQUENCE: 5
tgcttattgc agaccgtcaa tgatgtgctt ttggggggtca tatcgcatgg tctatccaag          60
tacgtaggtg ccaaatcaca caagggtaat caattcaaca a                           101

<210> SEQ ID NO 6
<211> LENGTH: 280
<212> TYPE: DNA
<213> ORGANISM: Spinacia oleracea

<400> SEQUENCE: 6
aggaagatca aatatgaaag acatttatag aaacagaaag ataaaaaagg aatggaggga          60
gtaattactg catagctggt tgttacggag tagttttctt tttatgcgtc aatgccctaa         120
taattgtcct ttcttttttcc ttttctagct ctgcagcaaa gccctcaagt cactgctatt         180
ctggttgtca atctacgcgg agtctcttgc ttacaggttg gttgcttatc gttaggtgaa         240
cacaaattca ccgaaaaggc tacatatacc ccatgggtat                             280

<210> SEQ ID NO 7
<211> LENGTH: 303
<212> TYPE: DNA
<213> ORGANISM: Spinacia oleracea

<400> SEQUENCE: 7
aagataaaaa aggaatggag ggagtaatta ctgcatagct ggttgttacg gagtagtttt          60
ctttttatgc gtcaatgccc taataattgt cctttctttt tccttttcta gctctgcagc         120

-continued

```
aaagccctca agtcactgct attctggttg tcaatctacg cggagtctct tgcttacagg      180
ttggttgctt atcgttaggt gaacacaaat tcaccgaaaa ggctacatat accccatggg      240
tatagaatag tgtcataccc tgggctgtga ttggtttaga tttataaatt ccatgtgggg      300
ttg                                                                    303

<210> SEQ ID NO 8
<211> LENGTH: 101
<212> TYPE: DNA
<213> ORGANISM: Spinacia oleracea

<400> SEQUENCE: 8
tactcattga gtatatgtat cagcttccca aattcgctgc tattatggtt gtcaatattc       60
catattttca tagtataaaa caagtgtggt attgtaacag g                         101

<210> SEQ ID NO 9
<211> LENGTH: 129
<212> TYPE: DNA
<213> ORGANISM: Spinacia oleracea

<400> SEQUENCE: 9
tgaaagtgaa ccctccgaaa tggcatcata ttccaccatt gaaggagctt gagtgttctt       60
cgaggatgcg cgagtaatag acttagtaag agcatcctta ttcttattcg gttgttttcc      120
agaagattt                                                             129

<210> SEQ ID NO 10
<211> LENGTH: 325
<212> TYPE: DNA
<213> ORGANISM: Spinacia oleracea

<400> SEQUENCE: 10
ccgtccctta atactcgacc cgttttgact ttttgcacta ttcacataat tcactttgac       60
cctattttat ttatagtgta tgaaaacgaa tgttagtata taatatattg ttggcttcat      120
cttaatatat attttcaaaa tattaatatt tttataagtt tttataatat gtacttaaaa      180
aaattagtga tcaaagttat gcattaacaa acgtgtccga tcaaaacaga tcaagtatta      240
agggacagag ggagtactac acgtctactc caaagtctca actagaagca aaaatggcca      300
accttagtag tgaaatcacg tggat                                            325

<210> SEQ ID NO 11
<211> LENGTH: 101
<212> TYPE: DNA
<213> ORGANISM: Spinacia oleracea

<400> SEQUENCE: 11
tcctattttc aaaatcacac atgaaaaatg atgatgagaa aaatctcact gcacttagtg       60
tttgaggacg ctaagacctc atattacctt attttaaatt a                         101

<210> SEQ ID NO 12
<211> LENGTH: 59
<212> TYPE: DNA
<213> ORGANISM: Spinacia oleracea

<400> SEQUENCE: 12
ttttcaggaa attgtcgatt ggaaaattaa tttacgtccc atttactctg ccagtatca        59

<210> SEQ ID NO 13
```

-continued

```
<211> LENGTH: 88
<212> TYPE: DNA
<213> ORGANISM: Spinacia oleracea

<400> SEQUENCE: 13
tgaactaaca ttttatacat ctacgtgatc taccattatg tgtatgaatg tggacctagg     60
gaagaaccta tcggttttca gtatggct                                        88

<210> SEQ ID NO 14
<211> LENGTH: 101
<212> TYPE: DNA
<213> ORGANISM: Spinacia oleracea

<400> SEQUENCE: 14
tatgtttgtg atgtcatttg aagtgtacaa ggtcatattt gcttcttttt taatatgtgg     60
cactgcacta gattcaattt gttatgaaac gaaattggtc g                        101

<210> SEQ ID NO 15
<211> LENGTH: 101
<212> TYPE: DNA
<213> ORGANISM: Spinacia oleracea

<400> SEQUENCE: 15
gtttggcatt ttgattgcca aattgcattt gatcaagtgg tatactggta tctgatgttt     60
acccccgcat tggctatctg attttattag ttccctaatg c                        101

<210> SEQ ID NO 16
<211> LENGTH: 300
<212> TYPE: DNA
<213> ORGANISM: Spinacia oleracea

<400> SEQUENCE: 16
gaaaaataag attccaaaat tattttttgaa ttaaaaaagt agggtgccac atagataaat    60
aattaggtgt cagatagata ttttattaat taattactaa tattatgcat atacaacttc   120
atcaaaaaac aagcactcta ataattaata attcaatcta aaataaaatt caatccaaaa   180
tcaaaaatca atctaatata atatataaaa tatagcagtt ggtatatcta gaagttttat   240
tttaacttaa caatttaatt aaatacgtgt attgcacggg ctaaaatcta gtacattata   300

<210> SEQ ID NO 17
<211> LENGTH: 101
<212> TYPE: DNA
<213> ORGANISM: Spinacia oleracea

<400> SEQUENCE: 17
aaattgactt ttaaaatcaa agaaatgaaa actgaatata atacaaaaca agttgtaagt     60
ggatgtctac taacttagtt ggtaaggtat tcagggatat t                        101

<210> SEQ ID NO 18
<211> LENGTH: 238
<212> TYPE: DNA
<213> ORGANISM: Spinacia oleracea

<400> SEQUENCE: 18
ccgtccaacc ctccgccggc gtcgcgtttg agagaggtaa gttttttcaaa aaaaaaaatt    60 aatttcattg ttgtgccgcc cagaaatggc gggtgaagcc atggttgtgc cgccttggat   120
aagcggtggc ggccatggtt ctgtcgcaga tcttgggtgg gtggaccatg ctgccgccg    180 cttatctagg gcggcacaac catggcttta cacgccattt ttgggcgtca gtcagcca     238
```

```
<210> SEQ ID NO 19
<211> LENGTH: 101
<212> TYPE: DNA
<213> ORGANISM: Spinacia oleracea

<400> SEQUENCE: 19
tcaatcttca ccatcttctc ctattttcct ttaagttacc acacaaagga aaactagttt        60
ataattgtgt tttcccttaa aaactgtttt tcatgaaaaa t                          101

<210> SEQ ID NO 20
<211> LENGTH: 101
<212> TYPE: DNA
<213> ORGANISM: Spinacia oleracea

<400> SEQUENCE: 20
agttagccgc caagtcgatg accttgtcat aatatttgta ctggatatta agtttctcag        60
atctggagca gtaactaaca tggcatccaa atgcttccac t                          101

<210> SEQ ID NO 21
<211> LENGTH: 101
<212> TYPE: DNA
<213> ORGANISM: Spinacia oleracea

<400> SEQUENCE: 21
agtcgagctt tgaccgactt gtgtcgaacc ggacatcgaa taattcgcga acagactcga        60
ctccttaaca acccttaagt actgatatac tctttgttgg t                          101

<210> SEQ ID NO 22
<211> LENGTH: 236
<212> TYPE: DNA
<213> ORGANISM: Spinacia oleracea

<400> SEQUENCE: 22
atcaacgtta attatcatta gtaaaattat taaactagtt aaccaaggca actaacaaga        60
tgcaaaatgt acaattgaga aggagaattc aaacatgcaa cctatcttac atagatttta       120
gtcttatttc ctccatattt taaaaaatac gctttaatta acacgtaatt ttaaaaaaat       180
gagttaaatt tattaaaata atataaaaat tgggtaaagg gtgaattatt tattaa          236
```

SPINACIA PLANT WITH LOW OXALIC ACID CONTENT

CROSS-REFERENCE TO RELATED APPLICATIONS

The present application is a 35 U.S.C. § 371 national stage application of International patent application PCT/JP2020/014904, filed Mar. 31, 2020. The entire content of this application is incorporated herein by reference.

FIELD

The present invention relates to a *spinacia* plant with a low oxalic acid content, in particular, a *spinacia* plant with a low oxalic acid content, a method for producing the same, a screening method, a primer or probe for the screening, and a kit for the screening.

BACKGROUND

Spinach is a plant that has a high content of oxalic acid. Oxalic acid binds to calcium in a body, and thus is considered to inhibit calcium absorption and cause calculus (stones) (Non-Patent Literatures 1 and 2).

Therefore, it is recommended that intakes of large amounts of foods with high contents of oxalic acid be avoided to prevent the calculus (Non-Patent Literature 3). According to a study conducted in the United States, it was reported that 40% of dietary intake of oxalic acid was derived from spinach, and that men and elderly women frequently eating spinach are prone to the calculus (Non-Patent Literature 4). In addition, oxalic acid is considered to be a causative substance of harsh taste, and therefore reducing oxalic acid concentration is an important problem (Non-Patent Literature 1).

In general, there are the following reports regarding the oxalic acid content of spinach: the content differs with seasons and is higher in winter than in summer (Non-Patent Literature 5); differences among varieties are smaller than the seasonal differences, and slow growing varieties have higher contents than fast growing varieties by small differences of approximately 20% (Non-Patent Literatures 5 and 6); the content is increased with the growth (Non-Patent Literature 1); leaf blades have higher contents than petioles (Non-Patent Literature 7); and there is no difference in the oxalic acid content between old and new varieties, and between OP varieties (open-pollinated varieties) and F1 (first filial) hybrid varieties (Non-Patent Literature 8).

Breeding of spinach cultivar with low oxalic acid contents has been attempted by mutational treatment of irradiation (Patent Literature 1) or chemical treatment (Non-patent Literature 10). Non-Patent Literature 9 describes capability of producing the spinach with the low oxalic acid content by increasing a ratio of ammonia nitrogen in a nitrogen fertilizer used in hydroponic cultivation of spinach.

CITATION LIST

Patent Literature

[Patent Literature 1] Japanese Patent Application Laid-open No. 2014-150763

[Non-Patent Literature 1] Akira Kagawa (1997) "Kohinsitsu horenso no saibaiseiri" (Cultivation physiology of high quality spinach), Ishizue-publishing Corp., 74-84 [Non- Patent Literature 2] Libert and Franceschi (1987) Oxalate in crop plants. J. Agric. Food Chem. 35, 926-938

[Non-Patent Literature 3] The Japanese Urological Association, The Japanese Society of Endourology, The Japanese Society of Urolithiasis Research (2013) "Guidelines for the diagnosis of urolithiasis 2013 edition" Kanehara & Co., Ltd., minds.jcqhc.or.jp/n/med/4/med0022/G0000634/0021

[Non-Patent Literature 4] Taylor and Curhan (2007) Oxalate intake and the risk for nephrolithiasis. J Am Soc Nephro 118:2198-2204

[Non-Patent Literature 5] Kaminishi and Kita (2006) Seasonal change of nitrate and oxalate concentration in relation to the growth rate of spinach cultivars. HortScience 41 (7): 1589-1595

[Non-Patent Literature 6] Kawazu et al. (2002) Varietal and seasonal differences in oxalate content of spinach. Scientia Horticarturae 97:203-210

[Non-Patent Literature 7] Elia et al. (1998) Nitrogen nutrition, yield and quality of spinach. J Sci Food Agric 76, 341-346

[Non-Patent Literature 8] Solberg et al. (2015) Nitrate and oxalate in germplasm collections of spinach and other leafy vegetables. Emirates Journal of Food and Agriculture 27 (9): 698-705

[Non-Patent Literature 9] Kazuko Mitsui (2006), "Horenso wo tsukuru hitobito Nihon horenso kiko 17 no saibaigenba kara" (Spinach cultivating people, Journey for Japanese spinach, from 17 cultivation sites), published by Seibundo-shinkosha.

[Non-Patent Literature 10] Murakami et al. (2009) Low-oxalate spinach mutant induced by chemical Mutagenesis. J. Japan. Soc. Hort. Sci. 78 (2): 180-184

SUMMARY

Technical Problem

However, practical spinach varieties with low oxalic acid contents have not been obtained so far. The mutants described in Non-Patent Literature 10 are very vulnerable and extremely difficult to cultivate. In addition, methods such as hydroponic cultivation of spinach described in Non-Patent Literature 9 are employed by only a few producers due to high costs and efforts required for management, and therefore are not considered to prevail. As a result, there are still no known spinach varieties that achieve oxalic acid contents less than half of the normal content or low oxalic acid contents even by general soil cultivation.

The object of the present invention is to provide a *spinacia* plant(s) with a low oxalic acid content, in particular, a *spinacia* plant(s) with a low oxalic acid content unaffected by environmental conditions, a method for producing the same, a screening method, and a screening kit.

Solution to Problem

The present invention provides the following invention:

[1] A *spinacia* plant with a low oxalic acid content comprising at least one low oxalic acid locus located in a chromosome 4 region.

[2] The *spinacia* plant with a low oxalic acid content according to [1], wherein the low oxalic acid locus is located at a part corresponding to Scaffold code LZYP01000033.1, a part corresponding to a genomic DNA fragment LZYP01001417.1, or a low oxalic acid locus at a part therebetween, in the chromosome 4 region.

[3] The *spinacia* plant with a low oxalic acid content according to [1] or [2], wherein the low oxalic acid locus is identified with a low oxalic acid SNP marker.

[4] The *spinacia* plant with a low oxalic acid content according to any one of [1] to [3], wherein the low oxalic acid locus is identified with at least one SNP marker(s) selected from the group consisting of the following (1) to (22):

(1) SL01: a polymorphism with substitution of T for the 28,543rd nucleotide A of Scaffold code LZYP01000033.1;

(2) SL208545: a polymorphism with substitution of T for the 208,545th nucleotide C of Scaffold code LZYP01000033.1;

(3) SL220275: a polymorphism with substitution of G for the 220,275th nucleotide C of Scaffold code LZYP01000033.1;

(4) SL241754: a polymorphism with substitution of A for the 241, 754th nucleotide C of Scaffold code LZYP01000033.1;

(5) SL293265: a polymorphism with substitution of T for the 293,265th nucleotide A of Scaffold code LZYP01000033.1;

(6) SL293658: a polymorphism with substitution of A for the 293,658th nucleotide G of Scaffold code LZYP01000033.1;

(7) SL293902: a polymorphism with substitution of A for the 293,902nd nucleotide G of Scaffold code LZYP01000033.1;

(8) SL294081: a polymorphism with substitution of G for the 294,081st nucleotide A of Scaffold code LZYP01000033.1;

(9) SL430237: a polymorphism with substitution of A for the 430,237th nucleotide G of Scaffold code LZYP01000033.1;

(10) SL747231: a polymorphism with substitution of A for the 747, 231st nucleotide G of Scaffold code LZYP01000033.1;

(11) SL759008: a polymorphism with substitution of G for the 759,008th nucleotide T of Scaffold code LZYP01000033.1;

(12) SL812367: a polymorphism with substitution of C for the 812, 367th nucleotide G of Scaffold code LZYP01000033.1;

(13) SL812384: a polymorphism with substitution of C for the 812, 384th nucleotide T of Scaffold code LZYP01000033.1;

(14) SL812514: a polymorphism with substitution of T for the 812, 514th nucleotide C of Scaffold code LZYP01000033.1;

(15) SL812601: a polymorphism with substitution of G for the 812, 601st nucleotide A of Scaffold code LZYP01000033.1;

(16) SL1252234: a polymorphism with substitution of C for the 1, 252, 234th nucleotide A of Scaffold code LZYP01000033.1;

(17) SL02: a polymorphism with substitution of T for the 1,847,918th nucleotide C of Scaffold code LZYP01000033.1;

(18) SL2167344: a polymorphism with substitution of T for the 2, 167, 344th nucleotide C of Scaffold code LZYP01000033.1;

(19) SL78812: a polymorphism with substitution of T for the 78,812nd nucleotide C of Scaffold code LZYP01001417.1;

(20) SL03: a polymorphism with substitution of A for the 90,490th nucleotide G of Scaffold code LZYP01001417.1;

(21) SL97243: a polymorphism with substitution of A for the 97, 243rd nucleotide G of Scaffold code LZYP01001417.1; and

(22) SL323336: a polymorphism with substitution of A for the 323, 336th nucleotide T of Scaffold code LZYP01001417.1.

[5] The *spinacia* plant with a low oxalic acid content according to [4], wherein the low oxalic acid locus is identified with at least one SNP marker selected from the group consisting of (1), (17) and (20).

[6] The *spinacia* plant with a low oxalic acid content according to any one of [1] to [5], wherein the low oxalic acid locus is identified with at least one polynucleotide selected from the group consisting of the following (1-1) to (22-2):

(1-1) a polynucleotide having a nucleotide sequence of SEQ ID NO: 1;

(1-2) a polynucleotide that has a mutation of at least one nucleotide other than the 57th nucleotide in the nucleotide sequence of SEQ ID NO: 1, 95% or more identity to the nucleotide sequence of SEQ ID NO: 1 and the same function as the polynucleotide having the nucleotide sequence of SEQ ID NO: 1;

(2-1) a polynucleotide having a nucleotide sequence of SEQ ID NO: 2;

(2-2) a polynucleotide that has a mutation of at least one nucleotide other than the 51st nucleotide in the nucleotide sequence of SEQ ID NO: 2, 95% or more identity to the nucleotide sequence of SEQ ID NO: 2 and the same function as the polynucleotide having the nucleotide sequence of SEQ ID NO: 2;

(3-1) a polynucleotide having a nucleotide sequence of SEQ ID NO: 3;

(3-2) a polynucleotide that has a mutation of at least one nucleotide other than the 135th nucleotide in the nucleotide sequence of SEQ ID NO: 3, 95% or more identity to the nucleotide sequence of SEQ ID NO: 3 and the same function as the polynucleotide having the nucleotide sequence of SEQ ID NO: 3;

(4-1) a polynucleotide having a nucleotide sequence of SEQ ID NO: 4;

(4-2) a polynucleotide that has a mutation of at least one nucleotide other than the 51st nucleotide in the nucleotide sequence of SEQ ID NO: 4, 95% or more identity to the nucleotide sequence of SEQ ID NO: 4 and the same function as the polynucleotide having the nucleotide sequence of SEQ ID NO: 4;

(5-1) a polynucleotide having a nucleotide sequence of SEQ ID NO: 5;

(5-2) a polynucleotide that has a mutation of at least one nucleotide other than the 51st nucleotide in the nucleotide sequence of SEQ ID NO: 5, 95% or more identity to the nucleotide sequence of SEQ ID NO: 5 and the same function as the polynucleotide having the nucleotide sequence of SEQ ID NO: 5;

(6-1) a polynucleotide having a nucleotide sequence of SEQ ID NO: 6;

(6-2) a polynucleotide that has a mutation of at least one nucleotide other than the 37th nucleotide in the nucleotide sequence of SEQ ID NO: 6, 95% or more identity to the nucleotide sequence of SEQ ID NO: 6 and the same function as the polynucleotide having the nucleotide sequence of SEQ ID NO: 6;

(7-1) a polynucleotide having a nucleotide sequence of SEQ ID NO: 7;

(7-2) a polynucleotide that has a mutation of at least one nucleotide other than the 244th nucleotide in the nucleotide sequence of SEQ ID NO: 7, 95% or more identity to the nucleotide sequence of SEQ ID NO: 7 and the same function as the polynucleotide having the nucleotide sequence of SEQ ID NO: 7;

(8-1) a polynucleotide having a nucleotide sequence of SEQ ID NO: 8;

(8-2) a polynucleotide that has a mutation of at least one nucleotide other than the 36th nucleotide in the nucleotide sequence of SEQ ID NO: 8, 95% or more identity to the nucleotide sequence of SEQ ID NO: 8 and the same function as the polynucleotide having the nucleotide sequence of SEQ ID NO: 8;

(9-1) a polynucleotide having a nucleotide sequence of SEQ ID NO: 9;

(9-2) a polynucleotide that has a mutation of at least one nucleotide other than the 81st nucleotide in the nucleotide sequence of SEQ ID NO: 9, 95% or more identity to the nucleotide sequence of SEQ ID NO: 9 and the same function as the polynucleotide having the nucleotide sequence of SEQ ID NO: 9;

(10-1) a polynucleotide having a nucleotide sequence of SEQ ID NO: 10;

(10-2) a polynucleotide that has a mutation of at least one nucleotide other than the 180th nucleotide in the nucleotide sequence of SEQ ID NO: 10, 95% or more identity to the nucleotide sequence of SEQ ID NO: 10 and the same function as the polynucleotide having the nucleotide sequence of SEQ ID NO: 10;

(11-1) a polynucleotide having a nucleotide sequence of SEQ ID NO: 11;

(11-2) a polynucleotide that has a mutation of at least one nucleotide other than the 51st nucleotide in the nucleotide sequence of SEQ ID NO: 11, 95% or more identity to the nucleotide sequence of SEQ ID NO: 11 and the same function as the polynucleotide having the nucleotide sequence of SEQ ID NO: 11;

(12-1) a polynucleotide having a nucleotide sequence of SEQ ID NO: 12;

(12-2) a polynucleotide that has a mutation of at least one nucleotide other than the 51st nucleotide in the nucleotide sequence of SEQ ID NO: 12, 95% or more identity to the nucleotide sequence of SEQ ID NO: 12 and the same function as the polynucleotide having the nucleotide sequence of SEQ ID NO: 12;

(13-1) a polynucleotide having a nucleotide sequence of SEQ ID NO: 13;

(13-2) a polynucleotide that has a mutation of at least one nucleotide other than the 9th nucleotide in the nucleotide sequence of SEQ ID NO: 13, 95% or more identity to the nucleotide sequence of SEQ ID NO: 13 and the same function as the polynucleotide having the nucleotide sequence of SEQ ID NO: 13;

(14-1) a polynucleotide having a nucleotide sequence of SEQ ID NO: 14;

(14-2) a polynucleotide that has a mutation of at least one nucleotide other than the 51st nucleotide in the nucleotide sequence of SEQ ID NO: 14, 95% or more identity to the nucleotide sequence of SEQ ID NO: 14 and the same function as the polynucleotide having the nucleotide sequence of SEQ ID NO: 14;

(15-1) a polynucleotide having a nucleotide sequence of SEQ ID NO: 15;

(15-2) a polynucleotide that has a mutation of at least one nucleotide other than the 5th nucleotide in the nucleotide sequence of SEQ ID NO: 15, 95% or more identity to the nucleotide sequence of SEQ ID NO: 15 and the same function as the polynucleotide having the nucleotide sequence of SEQ ID NO: 15;

(16-1) a polynucleotide having a nucleotide sequence of SEQ ID NO: 16;

(16-2) a polynucleotide that has a mutation of at least one nucleotide other than the 154th nucleotide in the nucleotide sequence of SEQ ID NO: 16, 95% or more identity to the nucleotide sequence of SEQ ID NO: 16 and the same function as the polynucleotide having the nucleotide sequence of SEQ ID NO: 16;

(17-1) a polynucleotide having a nucleotide sequence of SEQ ID NO: 17;

(17-2) a polynucleotide that has a mutation of at least one nucleotide other than the 12th nucleotide in the nucleotide sequence of SEQ ID NO: 17, 95% or more identity to the nucleotide sequence of SEQ ID NO: 17 and the same function as the polynucleotide having the nucleotide sequence of SEQ ID NO: 17;

(18-1) a polynucleotide having a nucleotide sequence of SEQ ID NO: 18;

(18-2) a polynucleotide that has a mutation of at least one nucleotide other than the 144th nucleotide in the nucleotide sequence of SEQ ID NO: 18, 95% or more identity to the nucleotide sequence of SEQ ID NO: 18 and the same function as the polynucleotide having the nucleotide sequence of SEQ ID NO: 18;

(19-1) a polynucleotide having a nucleotide sequence of SEQ ID NO: 19;

(19-2) a polynucleotide that has a mutation of at least one nucleotide other than the 91st nucleotide in the nucleotide sequence of SEQ ID NO: 19, 95% or more identity to the nucleotide sequence of SEQ ID NO: 19 and the same function as the polynucleotide having the nucleotide sequence of SEQ ID NO: 19;

(20-1) a polynucleotide having a nucleotide sequence of SEQ ID NO: 20;

(20-2) a polynucleotide that has a mutation of at least one nucleotide other than the 51st nucleotide in the nucleotide sequence of SEQ ID NO: 20, 95% or more identity to the nucleotide sequence of SEQ ID NO: 20 and the same function as the polynucleotide having the nucleotide sequence of SEQ ID NO: 20;

(21-1) a polynucleotide having a nucleotide sequence of SEQ ID NO: 21;

(21-2) a polynucleotide that has a mutation of at least one nucleotide other than the 51st nucleotide in the nucleotide sequence of SEQ ID NO: 21, 95% or more identity to the nucleotide sequence of SEQ ID NO: 21 and the same function as the polynucleotide having the nucleotide sequence of SEQ ID NO: 21;

(22-1) a polynucleotide having a nucleotide sequence of SEQ ID NO: 22; and (22-2) a polynucleotide that has a mutation of at least one nucleotide other than the 236th nucleotide in the nucleotide sequence of SEQ ID NO: 22, 95% or more identity to the nucleotide sequence of SEQ ID NO: 22 and the same function as the polynucleotide having the nucleotide sequence of SEQ ID NO: 22.

[7] The *spinacia* plant with a low oxalic acid content according to [6], wherein the low oxalic acid locus is identified with at least one polynucleotide selected from the group consisting of (1-1), (1-2), (17-1), (17-2), (20-1) and (20-2).

[8] The *spinacia* plant with a low oxalic acid content according to any one of [1] to [7], wherein the low oxalic acid locus is a low oxalic acid locus possessed by a *spinacia* (accession number: FERM BP-22384).

[9] The *spinacia* plant with a low oxalic acid content according to any one of [1] to [8], wherein the *spinacia* plant is a spinach (accession number: FERM BP-22384) or progeny of the spinach (accession number: FERM BP-22384).

[10] The *spinacia* plant with a low oxalic acid content according to any one of [1] to [9], wherein the *spinacia* plant is a plant body or a part of the plant body.

[11] The *spinacia* plant with a low oxalic acid content according to any one of [1] to [10], wherein the *spinacia* plant is a seed.

[12] The *spinacia* plant with a low oxalic acid content according to any one of [1] to [11], wherein the *spinacia* plant is at least one selected from a plant cell, a tissue and an organ.

[13] The *spinacia* plant with a low oxalic acid content according to any one of [1] to [12], wherein the *spinacia* plant fulfills at least one of an oxalic acid content of 600 mg/100 g FW or less at a tip of a leaf blade, and an oxalic acid content of 400 mg/100 g FW or less at an edible portion.

[14] A method for producing a *spinacia* plant with a low oxalic acid content, the method comprising at least a step of cross breeding the *spinacia* plant with a low oxalic acid ontent according to any one of [1] to with another *spinacia* plant.

[15] The method according to [14], the method further comprising a step of selecting a plant having at least one low oxalic acid locus in the chromosome 4 region from a *spinacia* plant obtained at the step of cross breeding or progeny of the *spinacia* plant.

[16] The method according to [15], wherein the plant having a low oxalic acid locus is selected by using at least one SNP marker selected from the group consisting of the above (1) to (22).

[17] The method according to or [16], wherein the plant having the low oxalic acid locus is selected depending on presence or absence of at least one polynucleotide selected from the group consisting of the above (1-1) to (22-2) at the step of selecting.

[18] A method for screening *spinacia* plants with low oxalic acid contents, the method comprising selecting a *spinacia* plant having at least one low oxalic acid locus located in a chromosome 4 region.

[19] The method according to [18], the method comprising selecting the plant having the low oxalic acid locus by using at least one SNP marker selected from the group consisting of the above (1) to (22):

[20] The method according to or [19], the method comprising selecting the plant having the low oxalic acid locus depending on presence or absence of at least one polynucleotide selected from the group consisting of the above (1-1) to (22-2).

[21] A kit for screening *spinacia* plants with low oxalic acid contents, the kit comprising at least a primer or a probe for screening *spinacia* plants with low oxalic acid, the primer or the probe being specifically bound to at least a portion of at least one low oxalic acid locus located in a portion(s) corresponding to genomic DNA fragments of Scaffold codes LZYP01000033.1 and LZYP01001417.1.

Advantageous Effects of Invention

According to the present invention, *spinacia* plants with low oxalic acid contents can be obtained stably without being affected by environmental conditions. A production method for efficiently producing the *spinacia* plant(s) with a low oxalic acid content(s), is also provided. Furthermore, a method and a kit for efficiently screening the *spinacia* plant(s) with a low oxalic acid content(s) from among various *spinacia* plants, are provided.

DESCRIPTION OF EMBODIMENTS

The invention is described in detail below. In the following explanation, "%" indicates "weight %" unless otherwise explained.

[*Spinacia* Plant with Low Oxalic Acid Content]

In the present invention, a *spinacia* plant(s) with a low oxalic acid content has a low oxalic acid locus.

(*Spinacia* Plant)

In this description, the *spinacia* plant(s) refers to all plants belonging to genus *Spinacia*, which belong to the Chenopodiaceae subfamily in the Amaranthaceae family, such as Spinach (*Spinacia oleracea*). The origin, variety, and sowing season (sowing in fall or spring) are not particularly limited. The *spinacia* plant(s) may refer to a plant body or a part(s) thereof. Examples of the plant body part include leaves, stems, flowers, roots, seeds, and combinations of two or more thereof. The plant body part preferably includes at least an edible part (e.g., leave, stem, and combinations thereof) or is the seed. The plant body part may refer to cells, tissues or organs of the *spinacia* plant. Their origins are not particularly limited. For example, they may be extracted directly from the *spinacia* plant, or the plant body part may be obtained by culturing them.

(Low Oxalic Acid Content)

In this description, the low oxalic acid content and the low oxalic acid refer to the oxalic acid content of *spinacia* plant lower than those of normal *spinacia* plants. Preferably, the oxalic acid content fulfills either one or both of 600 mg/100 g FW or less at a tip of leaf blade, and 400 mg/100 g FW or less in the edible part (the whole part including leaf blade and petiole). The oxalic acid content can be determined by the HPLC method. The timing of the measurement is not particularly limited. In the case of the oxalic acid content at the tip of leaf blade, the timing is not particularly limited, as long as a 300 mg sample can be taken from the leaf blade of one main leaf. In the case of the oxalic acid content of the edible part, it is not particularly limited as long as the edible part can be harvested. In this description, the high oxalic acid content or the high oxalic acid refers to the oxalic acid content of the *spinacia* plant equal to or higher than those of normal *spinacia* plants (not low oxalic acid content).

(Low Oxalic Acid Locus)

In the present invention, at least one of the low oxalic acid locus (loci) possessed by the *spinacia* plant(s) with a low oxalic acid content(s) is a low oxalic acid locus in a chromosome 4 region. Preferably, the low oxalic acid locus is located at a part corresponding to a genomic DNA fragment with Scaffold code LZYP01000033.1, a part corresponding to a genomic DNA fragment LZYP01001417.1, and a part therebetween in the chromosome 4 region, and more preferably located at the part corresponding to the genomic DNA fragment with Scaffold code LZYP01000033.1, and the part corresponding to the genomic DNA fragment LZYP01001417.1. Information including sequences of the genomic DNA fragments with Scaffold codes LZYP01000033.1 and LZYP01001417.1 is available in the NCBI database ncbi.nlm.nih.gov/nuccore/LZYP01000033.1?report=fasta; ncbi.nlm.nih.gov/nuccore/LZYP01001417.1?report=fasta; and ncbi.nlm.nih.gov/

Traces/wgs/LZYP01? (display=contigs). Examples of methods for confirming the corresponding position of chromosome 4 of the *spinacia* plant include a query to a public database of genomes of *spinacia* plants (e.g., use of BLAST® search page of SpinachBase: spinachbase.org/?q=blast).

The *spinacia* plant with the low oxalic acid content may have one or more low oxalic acid locus (loci) located in the chromosome 4 region. The *spinacia* plant has the low oxalic acid locus located in the chromosome 4 region, and may have a locus (loci) located in chromosome region(s) other than chromosome 4 (e.g., any of chromosomes 1 through 6). In addition to the low oxalic acid locus located in the chromosome 4 region, the *spinacia* plant may have a low oxalic acid locus (loci) in other chromosome regions.

Examples of the low oxalic acid locus include loci identified with a genetic marker such as single nucleotide polymorphisms (SNPs), simple repetitive sequences (microsatellites, SSRs), insertions/deletions (InDel), and sequence tagging sites (STSs). The locus identified with the SNP marker is preferred.

Examples of the SNP marker to identify the low oxalic acid locus include the following (1) to (22). The *spinacia* plant with the low oxalic acid content preferably has a specific polymorphism identified by at least one of (1) to (22). In other words, the *spinacia* plant with the low oxalic acid content can be confirmed when having at least one of polymorphisms (1) to (22).

(1) SL01: A polymorphism with substitution of T for the 28, 543rd nucleotide A of Scaffold code LZYP01000033.1.

(2) SL208545: A polymorphism with substitution of T for the 208,545th nucleotide C of Scaffold code LZYP01000033.1.

(3) SL220275: A polymorphism with substitution of G for the 220,275th nucleotide C of Scaffold code LZYP01000033.1.

(4) SL241754: A polymorphism with substitution of A for the 241,754th nucleotide C of Scaffold code LZYP01000033.1.

(5) SL293265: A polymorphism with substitution of T for the 293,265th nucleotide A of Scaffold code LZYP01000033.1.

(6) SL293658: A polymorphism with substitution of A for the 293,658th nucleotide G of Scaffold code LZYP01000033.1.

(7) SL293902: A polymorphism with substitution of A for the 293,902nd nucleotide G of Scaffold code LZYP01000033.1.

(8) SL294081: A polymorphism with substitution of G for the 294,081st nucleotide A of Scaffold code LZYP01000033.1.

(9) SL430237: A polymorphism with substitution of A for the 430,237th nucleotide G of Scaffold code LZYP01000033.1.

(10) SL747231: A polymorphism with substitution of A for the 747, 231st nucleotide G of Scaffold code LZYP01000033.1.

(11) SL759008: A polymorphism with substitution of G for the 759,008th nucleotide T of Scaffold code LZYP01000033.1.

(12) SL812367: A polymorphism with substitution of C for the 812, 367th nucleotide G of Scaffold code LZYP01000033.1.

(13) SL812384: A polymorphism with substitution of C for the 812, 384th nucleotide T of Scaffold code LZYP01000033.1.

(14) SL812514: A polymorphism with substitution of T for the 812, 514th nucleotide C of Scaffold code LZYP01000033.1.

(15) SL812601: A polymorphism with substitution of G for the 812, 601st nucleotide A of Scaffold code LZYP01000033.1.

(16) SL1252234: A polymorphism with substitution of C for the 1, 252, 234th nucleotide A of Scaffold code LSYP01000033.1.

(17) SL02: A polymorphism with substitution of T for the 1,847,918th nucleotide C of Scaffold code LZYP01000033.1.

(18) SL2167344: A polymorphism with substitution of T for the 2, 167, 344th nucleotide C of Scaffold code LZYP01000033.1.

(19) SL78812: A polymorphism with substitution of T for the 78,812nd nucleotide C of Scaffold code LZYP01001417.1.

(20) SL03: A polymorphism with substitution of A for the 90,490th nucleotide G of Scaffold code LZYP01001417.1.

(21) SL97243: A polymorphism with substitution of A for the 97,243rd nucleotide G of Scaffold code LZYP01001417.1.

(22) SL323336: A polymorphism with substitution of A for the 323, 336th nucleotide T of Scaffold code LZYP01001417.1.

Examples of the methods for confirming the corresponding position of chromosome 4 of the *spinacia* plants (1) to (22) include queries to the aforementioned NCBI database or the public database of genomes of *spinacia* plants. The SNP marker is at least one selected from the group consisting of aforementioned (1) to (22), and can be a combination of two or more thereof. The SNP marker preferably includes at least one selected from (1), (17) and (20), and more preferably includes at least one of (1) and (20).

On the other hand, the low oxalic acid locus may be identified with the following (1-1) to (22-2) polynucleotides. The *spinacia* plant with the low oxalic acid content preferably has at least one of (1-1) to (22-2). In other words, the *spinacia* plant with the low oxalic acid content can be confirmed when having at least one of polynucleotides (1-1) to (22-2).

(1-1) A Polynucleotide Having a Nucleotide Sequence of SEQ ID NO: 1

(1-2) A polynucleotide that has a mutation of at least one nucleotide other than the 57th nucleotide in the nucleotide sequence of SEQ ID NO: 1, 95% or more identity to the nucleotide sequence of SEQ ID NO: 1 and the same function as the polynucleotide having the nucleotide sequence of SEQ ID NO: 1.

The 57th nucleotide T in the nucleotide sequence of SEQ ID NO: 1 corresponds to the SNP marker of the above (1). When the 57th nucleotide in the nucleotide sequence of SEQ ID NO: 1 is T, the *spinacia* plant has a low oxalic acid content. When the 57th nucleotide is not T while there is no other low oxalic acid locus, the *spinacia* plant has a high oxalic acid content.

(2-1) A Polynucleotide Having a Nucleotide Sequence of SEQ ID NO: 2

(2-2) A polynucleotide that has a mutation of at least one nucleotide other than the 51st nucleotide in the nucleotide sequence of SEQ ID NO: 2, 95% or more identity to the nucleotide sequence of SEQ ID NO: 2 and the same function as the polynucleotide having the nucleotide sequence of SEQ ID NO: 2.

The 51st nucleotide T in the nucleotide sequence of SEQ ID NO: 2 corresponds to the SNP marker of the above (2). When the 51st nucleotide in the nucleotide sequence of SEQ ID NO: 2 is T, the *spinacia* plant has a low oxalic acid content. When the 51st nucleotide is not T while there is no other low oxalic acid locus, the *spinacia* plant has a high oxalic acid content.

(3-1) A Polynucleotide Having a Nucleotide Sequence of SEQ ID NO: 3

(3-2) A polynucleotide that has a mutation of at least one nucleotide other than the 135th nucleotide in the nucleotide sequence of SEQ ID NO: 3, 95% or more identity to the nucleotide sequence of SEQ ID NO: 3 and the same function as the polynucleotide having the nucleotide sequence of SEQ ID NO: 3.

The 135th nucleotide G in the nucleotide sequence of SEQ ID NO: 3 corresponds to the SNP marker of the above (3). When the 135th nucleotide in the nucleotide sequence of SEQ ID NO: 3 is G, the *spinacia* plant has a low oxalic acid content. When the 135th nucleotide is not G while there is no other low oxalic acid locus, the *spinacia* plant has a high oxalic acid content.

(4-1) A Polynucleotide Having a Nucleotide Sequence of SEQ ID NO: 4

(4-2) A polynucleotide that has a mutation of at least one nucleotide other than the 51st nucleotide in the nucleotide sequence of SEQ ID NO: 4, 95% or more identity to the nucleotide sequence of SEQ ID NO: 4 and the same function as the polynucleotide having the nucleotide sequence of SEQ ID NO: 4.

The 51st nucleotide A in the nucleotide sequence of SEQ ID NO: 4 corresponds to the SNP marker of the above (4). When the 51st nucleotide in the nucleotide sequence of SEQ ID NO: 4 is A, the *spinacia* plant has a low oxalic acid content. When the 51st nucleotide is not A while there is no other low oxalic acid locus, the *spinacia* plant has a high oxalic acid content.

(5-1) A Polynucleotide Having a Nucleotide Sequence of SEQ ID NO: 5

(5-2) A polynucleotide that has a mutation of at least one nucleotide other than the 51st nucleotide in the nucleotide sequence of SEQ ID NO: 5, 95% or more identity to the nucleotide sequence of SEQ ID NO: 5 and the same function as the polynucleotide having the nucleotide sequence of SEQ ID NO: 5.

The 51st nucleotide T in the nucleotide sequence of SEQ ID NO: 5 corresponds to the SNP marker of the above (5). When the 51st nucleotide in the nucleotide sequence of SEQ ID NO: 5 is T, the *spinacia* plant has a low oxalic acid content. When the 51st nucleotide is not T while there is no other low oxalic acid locus, the *spinacia* plant has a high oxalic acid content.

(6-1) A Polynucleotide Having a Nucleotide Sequence of SEQ ID NO: 6

(6-2) A polynucleotide that has a mutation of at least one nucleotide other than the 37th nucleotide in the nucleotide sequence of SEQ ID NO: 6, 95% or more identity to the nucleotide sequence of SEQ ID NO: 6 and the same function as the polynucleotide having the nucleotide sequence of SEQ ID NO: 6.

The 37th nucleotide A in the nucleotide sequence of SEQ ID NO: 6 corresponds to the SNP marker of the above (6). When the 37th nucleotide in the nucleotide sequence of SEQ ID NO: 6 is A, the *spinacia* plant has a low oxalic acid content. When the 37th nucleotide is not A while there is no other low oxalic acid locus, the *spinacia* plant has a high oxalic acid content.

(7-1) A Polynucleotide Having a Nucleotide Sequence of SEQ ID NO: 7

(7-2) A polynucleotide that has a mutation of at least one nucleotide other than the 244th nucleotide in the nucleotide sequence of SEQ ID NO: 7, 95% or more identity to the nucleotide sequence of SEQ ID NO: 7 and the same function as the polynucleotide having the nucleotide sequence of SEQ ID NO: 7.

The 244th nucleotide A in the nucleotide sequence of SEQ ID NO: 7 corresponds to the SNP marker of the above (7). When the 244th nucleotide in the nucleotide sequence of SEQ ID NO: 7 is A, the *spinacia* plant has a low oxalic acid content. When the 244th nucleotide is not A while there is no other low oxalic acid locus, the *spinacia* plant has a high oxalic acid content.

(8-1) A Polynucleotide Having a Nucleotide Sequence of SEQ ID NO: 8

(8-2) A polynucleotide that has a mutation of at least one nucleotide other than the 36th nucleotide in the nucleotide sequence of SEQ ID NO: 8, 95% or more identity to the nucleotide sequence of SEQ ID NO: 8 and the same function as the polynucleotide having the nucleotide sequence of SEQ ID NO: 8.

The 36th nucleotide G in the nucleotide sequence of SEQ ID NO: 8 corresponds to the SNP marker of the above (8). When the 36th nucleotide in the nucleotide sequence of SEQ ID NO: 8 is G, the *spinacia* plant has a low oxalic acid content. When the 36th nucleotide is not G while there is no other low oxalic acid locus, the *spinacia* plant has a high oxalic acid content.

(9-1) A Polynucleotide Having a Nucleotide Sequence of SEQ ID NO: 9

(9-2) A polynucleotide that has a mutation of at least one nucleotide other than the 81st nucleotide in the nucleotide sequence of SEQ ID NO: 9, 95% or more identity to the nucleotide sequence of SEQ ID NO: 9 and the same function as the polynucleotide having the nucleotide sequence of SEQ ID NO: 9.

The 81st nucleotide A in the nucleotide sequence of SEQ ID NO: 9 corresponds to the SNP marker of the above (9). When the 81st nucleotide in the nucleotide sequence of SEQ ID NO: 9 is A, the *spinacia* plant has a low oxalic acid content. When the 81st nucleotide is not A while there is no other low oxalic acid locus, the *spinacia* plant has a high oxalic acid content.

(10-1) A Polynucleotide Having a Nucleotide Sequence of SEQ ID NO: 10

(10-2) A polynucleotide that has a mutation of at least one nucleotide other than the 180th nucleotide in the nucleotide sequence of SEQ ID NO: 10, 95% or more identity to the nucleotide sequence of SEQ ID NO: 10 and the same function as the polynucleotide having the nucleotide sequence of SEQ ID NO: 10.

The 180th nucleotide A in the nucleotide sequence of SEQ ID NO: 10 corresponds to the SNP marker of the above (10). When the 180th nucleotide in the nucleotide sequence of SEQ ID NO: 10 is A, the *spinacia* plant has a low oxalic acid content. When the 180th nucleotide is not A while there is no other low oxalic acid locus, the *spinacia* plant has a high oxalic acid content.

(11-1) A Polynucleotide Having a Nucleotide Sequence of SEQ ID NO: 11

(11-2) A polynucleotide that has a mutation of at least one nucleotide other than the 51st nucleotide in the nucleotide sequence of SEQ ID NO: 11, 95% or more identity to the nucleotide sequence of SEQ ID NO: 11 and the same function as the polynucleotide having the nucleotide sequence of SEQ ID NO: 11.

The 51st nucleotide G in the nucleotide sequence of SEQ ID NO: 11 corresponds to the SNP marker of the above (11). When the 51st nucleotide in the nucleotide sequence of SEQ ID NO: 11 is G, the *spinacia* plant has a low oxalic acid content. When the 51st nucleotide is not G while there is no other low oxalic acid locus, the *spinacia* plant has a high oxalic acid content.

(12-1) A Polynucleotide Having a Nucleotide Sequence of SEQ ID NO: 12

(12-2) A polynucleotide that has a mutation of at least one nucleotide other than the 51st nucleotide in the nucleotide sequence of SEQ ID NO: 12, 95% or more identity to the nucleotide sequence of SEQ ID NO: 12 and the same function as the polynucleotide having the nucleotide sequence of SEQ ID NO: 12.

The 51st nucleotide C in the nucleotide sequence of SEQ ID NO: 12 corresponds to the SNP marker of the above (12). When the 51st nucleotide in the nucleotide sequence of SEQ ID NO: 12 is C, the *spinacia* plant has a low oxalic acid content. When the 51st nucleotide is not C while there is no other low oxalic acid locus, the *spinacia* plant has a high oxalic acid content.

(13-1) A Polynucleotide Having a Nucleotide Sequence of SEQ ID NO: 13

(13-2) A polynucleotide that has a mutation of at least one nucleotide other than the 9th nucleotide in the nucleotide sequence of SEQ ID NO: 13, 95% or more identity to the nucleotide sequence of SEQ ID NO: 13 and the same function as the polynucleotide having the nucleotide sequence of SEQ ID NO: 13.

The 9th nucleotide C in the nucleotide sequence of SEQ ID NO: 13 corresponds to the SNP marker of the above (13). When the 9th nucleotide in the nucleotide sequence of SEQ ID NO: 13 is C, the *spinacia* plant has a low oxalic acid content. When the 9th nucleotide is not C while there is no other low oxalic acid locus, the *spinacia* plant has a high oxalic acid content.

(14-1) A Polynucleotide Having a Nucleotide Sequence of SEQ ID NO: 14

(14-2) A polynucleotide that has a mutation of at least one nucleotide other than the 51st nucleotide in the nucleotide sequence of SEQ ID NO: 14, 95% or more identity to the nucleotide sequence of SEQ ID NO: 14 and the same function as the polynucleotide having the nucleotide sequence of SEQ ID NO: 14.

The 51st nucleotide T in the nucleotide sequence of SEQ ID NO: 14 corresponds to the SNP marker of the above (14). When the 51st nucleotide in the nucleotide sequence of SEQ ID NO: 14 is T, the *spinacia* plant has a low oxalic acid content. When the 51st nucleotide is not T while there is no other low oxalic acid locus, the *spinacia* plant has a high oxalic acid content.

(15-1) A Polynucleotide Having a Nucleotide Sequence of SEQ ID NO: 15

(15-2) A polynucleotide that has a mutation of at least one nucleotide other than the 5th nucleotide in the nucleotide sequence of SEQ ID NO: 15, 95% or more identity to the nucleotide sequence of SEQ ID NO: 15 and the same function as the polynucleotide having the nucleotide sequence of SEQ ID NO: 15.

The 5th nucleotide G in the nucleotide sequence of SEQ ID NO: 15 corresponds to the SNP marker of the above (15). When the 5th nucleotide in the nucleotide sequence of SEQ ID NO: 15 is G, the *spinacia* plant has a low oxalic acid content. When the 5th nucleotide is not G while there is no other low oxalic acid locus, the *spinacia* plant has a high oxalic acid content.

(16-1) A Polynucleotide Having a Nucleotide Sequence of SEQ ID NO: 16

(16-2) A polynucleotide that has a mutation of at least one nucleotide other than the 154th nucleotide in the nucleotide sequence of SEQ ID NO: 16, 95% or more identity to the nucleotide sequence of SEQ ID NO: 16 and the same function as the polynucleotide having the nucleotide sequence of SEQ ID NO: 16.

The 154th nucleotide C in the nucleotide sequence of SEQ ID NO: 16 corresponds to the SNP marker of the above (16). When the 154th nucleotide in the nucleotide sequence of SEQ ID NO: 16 is C, the *spinacia* plant has a low oxalic acid content. When the 154th nucleotide is not C while there is no other low oxalic acid locus, the *spinacia* plant has a high oxalic acid content.

(17-1) A Polynucleotide Having a Nucleotide Sequence of SEQ ID NO: 17

(17-2) A polynucleotide that has a mutation of at least one nucleotide other than the 12th nucleotide in the nucleotide sequence of SEQ ID NO: 17, 95% or more identity to the nucleotide sequence of SEQ ID NO: 17 and the same function as the polynucleotide having the nucleotide sequence of SEQ ID NO: 17.

The 12th nucleotide T in the nucleotide sequence of SEQ ID NO: 17 corresponds to the SNP marker of the above (17). When the 12th nucleotide in the nucleotide sequence of SEQ ID NO: 17 is T, the *spinacia* plant has a low oxalic acid content. When the 12th nucleotide is not T while there is no other low oxalic acid locus, the *spinacia* plant has a high oxalic acid content.

(18-1) A Polynucleotide Having a Nucleotide Sequence of SEQ ID NO: 18

(18-2) A polynucleotide that has a mutation of at least one nucleotide other than the 144th nucleotide in the nucleotide sequence of SEQ ID NO: 18, 95% or more identity to the nucleotide sequence of SEQ ID NO: 18 and the same function as the polynucleotide having the nucleotide sequence of SEQ ID NO: 18.

The 144th nucleotide T in the nucleotide sequence of SEQ ID NO: 18 corresponds to the SNP marker of the above (18). When the 144th nucleotide in the nucleotide sequence of SEQ ID NO: 18 is T, the *spinacia* plant has a low oxalic acid content. When the 144th nucleotide is not T while there is no other low oxalic acid locus, the *spinacia* plant has a high oxalic acid content.

(19-1) A Polynucleotide Having a Nucleotide Sequence of SEQ ID NO: 19

(19-2) A polynucleotide that has a mutation of at least one nucleotide other than the 91st nucleotide in the nucleotide sequence of SEQ ID NO: 19, 95% or more identity to the nucleotide sequence of SEQ ID NO: 19 and the same function as the polynucleotide having the nucleotide sequence of SEQ ID NO: 19.

The 91st nucleotide T in the nucleotide sequence of SEQ ID NO: 19 corresponds to the SNP marker of the above (19). When the 91st nucleotide in the nucleotide sequence of SEQ ID NO: 19 is T, the *spinacia* plant has a low oxalic acid content. When the 91st nucleotide is not T while there is no other low oxalic acid locus, the *spinacia* plant has a high oxalic acid content.

(20-1) A Polynucleotide Having a Nucleotide Sequence of SEQ ID NO: 20

(20-2) A polynucleotide that has a mutation of at least one nucleotide other than the 51st nucleotide in the nucleotide sequence of SEQ ID NO: 20, 95% or more identity to the nucleotide sequence of SEQ ID NO: 20 and the same function as the polynucleotide having the nucleotide sequence of SEQ ID NO: 20.

The 51st nucleotide A in the nucleotide sequence of SEQ ID NO: 20 corresponds to the SNP marker of the above (20). When the 51st nucleotide in the nucleotide sequence of SEQ ID NO: 20 is A, the *spinacia* plant has a low oxalic acid content. When the 51st nucleotide is not A while there is no other low oxalic acid locus, the *spinacia* plant has a high oxalic acid content.

(21-1) A Polynucleotide Having a Nucleotide Sequence of SEQ ID NO: 21

(21-2) A polynucleotide that has a mutation of at least one nucleotide other than the 51st nucleotide in the nucleotide sequence of SEQ ID NO: 21, 95% or more identity to the nucleotide sequence of SEQ ID NO: 21 and the same function as the polynucleotide having the nucleotide sequence of SEQ ID NO: 21.

The 51st nucleotide A in the nucleotide sequence of SEQ ID NO: 21 corresponds to the SNP marker of the above (21). When the 51st nucleotide in the nucleotide sequence of SEQ ID NO: 21 is A, the *spinacia* plant has a low oxalic acid content. When the 51st nucleotide is not A while there is no other low oxalic acid locus, the *spinacia* plant has a high oxalic acid content.

(22-1) A Polynucleotide Having a Nucleotide Sequence of SEQ ID NO: 22

(22-2) A polynucleotide that has a mutation of at least one nucleotide other than the 236th nucleotide in the nucleotide sequence of SEQ ID NO: 22, 95% or more identity to the nucleotide sequence of SEQ ID NO: 22 and the same function as the polynucleotide having the nucleotide sequence of SEQ ID NO: 22.

The 236th nucleotide A in the nucleotide sequence of SEQ ID NO: 22 corresponds to the SNP marker of the above (22). When the 236th nucleotide in the nucleotide sequence of SEQ ID NO: 22 is A, the *spinacia* plant has a low oxalic acid content. When the 236th nucleotide is not A while there is no other low oxalic acid locus, the *spinacia* plant has a high oxalic acid content.

Examples of the methods for confirming the corresponding position of chromosome 4 of the *spinacia* plants (1-1) to (22-2) include queries to the aforementioned NCBI database or the public database of genomes of *spinacia* plants. Each of the polynucleotides refers also to polynucleotides having nucleotide sequences complementary to the nucleotide sequence identifying each polynucleotide.

The sequence having 95% or more identity to the nucleotide sequence for each polynucleotide refers to nucleotide sequences that correspond to variations in nucleotide sequences among plant species of *spinacia* plants, preferably varieties thereof. The identity is preferably 96% or more, 97% or more, or 98% or more, or more preferably 99% or more. The sequence with 90% or more identity to each sequence may refer to sequences that contain several (for example, 1 to 10, preferably 1 to 5, and more preferably 1, 2 or 3) nucleotide modifications (substitutions, deletions, insertions, additions, etc.) in each sequence. The nucleotide sequences of the corresponding locations in the *spinacia* plant species are obvious to those skilled in the art in the relevant technical field. For example, it can be determined by decoding the nucleotide sequence of the corresponding region in the *spinacia* plant or by referring to a database in which genetic information of *spinacia* plants are registered.

Identification analysis can be performed using algorithms such as BLAST®, or programs such as BLASTN® or BLASTX®.

Preferred examples of the *spinacia* plant with the low oxalic acid content include spinach (*Spinacia oleracea*) FERM BP-22384 and its progeny. The spinach FERM BP-22384 has been internationally deposited as seeds under the Budapest Treaty with International Accession Number FERM BP-22384 dated on Dec. 24, 2019 in National Institute of Technology and Evaluation, Biotechnology Center, International Patent Organism Depositary (NITE-IPOD: #120, 2-5-8 Kazusakamatari, Kisarazu-shi, Chiba, Japan, 292-0818).

The conditions for growing the *spinacia* plant with the low oxalic acid content are not particularly limited but same as conditions for growing normal *spinacia* plants. Other treatments (e.g., temperature, humidity control and selections of seasons for sowing) may be employed to improve fast growing, yield, and bolting. Spinach is harvested when it reaches 20 to 30 cm in height before bolting, because the petiole and leaf blade are generally edible. As the bolting is prompted by long daytime condition, a late bolting variety is selected for sowing in spring or summer in order to avoid the bolting. It generally germinates approximately five days after sowing, but the number of days elapsed until the harvest time differs greatly depending on seasons. For example, under the optimal growth temperature (15 to 25° C.), it takes approximately 30 days to reach the harvest time, but it is not limited to this.

[Method for Producing *Spinacia* Plant with Low Oxalic Acid Content]

Secondly, the present invention provides a method for producing a *spinacia* plant(s) with a low oxalic acid content. The production method includes at least a cross breeding step and may further include a selection step. Each step is explained below.

(Cross Breeding Step)

The cross breeding step is a step of cross breeding a *spinacia* plant with a low oxalic acid content with another *spinacia* plant. The *spinacia* plant with the low oxalic acid content is described in the previous section. Another *spinacia* plant may or may not be the above *spinacia* plant with the low oxalic acid content, and are not particularly limited. The method of cross breeding plant can be employed according to conventional methods.

(Selection Step)

The selection step is a step of selecting the plant having at least one low oxalic acid locus in the chromosome 4 region from the *spinacia* plants obtained in the cross breeding step or progeny line thereof. The low oxalic acid locus is explained in the previous section.

For the selection, the means of confirming that the *spinacia* plant has low oxalic acid locus is an ordinary means of marker analysis. Examples of the means include PCR method (e.g., PCR-RFLP, etc.), invader method, TaqMan method, single nucleotide extension method, pyrosequencing method, DigiTag2 method, Luminex method, direct sequencing method, LAMP method, microarray method, exonuclease cycling assay method. The means is preferably PCR method, more preferably PCR-RFLP method. For the confirmation by PCR method, it is sufficient to use a primer(s) or probe(s) that allows detection of at least one SNP marker selected from the group consisting of (1) to (22) mentioned above, or a primer(s) or probe(s) that allows detection of at least one polynucleotide selected from the group consisting of (1-1) to (22-2) mentioned above. The nucleotide sequences of the primer and probe can be designed as appropriate according to a conventional method from nucleotide sequences proximity to the polymorphisms of (1) to (22) described above, or from nucleotide sequences proximity to the nucleotides of aforementioned (1-1) to (22-2) corresponding to the polymorphisms of (1) to (22). The number of nucleotide residues (nucleotide residues in a complementary portion in which a target site is annealed) constituting the primer and probe may be, for example, 15 or more, 16 or more, 17 or more, 18 or more, or 20 or more. The maximum thereof may be, for example, 50 or less, 40 or less, or 30 or less, but is not particularly limited. In the case of primer, it is sufficient to anneal the target site and specifically amplify an aimed product. The probe and primer may be labeled with fluorescent substances (e.g., 6-FAM, VIC, NED, PET) as needed, in terms of detection of amplified products and the like.

The timing of the selection step is not particularly limited as long as it is at a stage when a sample can be collected from the plant body. Therefore, the selection step may be performed after harvesting or when the plant has grown to such an extent that the sample may be collected before harvesting. It is sufficient that the cross breeding and selection steps are performed at least once as one cycle, and may be repeated two or more times.

[Method for Screening *Spinacia* Plant with Low Oxalic Acid Content]

Thirdly, the present invention provides a method for screening *spinacia* plants with low oxalic acid contents. In the screening method, the *spinacia* plant having at least one low oxalic acid locus in the chromosome 4 region is selected. A condition for the selection is same as that explained in the selection step of the production method.

[Kit for Selecting *Spinacia* Plant with Low Oxalic Acid Content]

Fourthly, the present invention provides a kit for selecting *spinacia* plant(s) with a low oxalic acid content(s). The kit contains a primer or probe capable of being specifically bound to a nucleotide portion containing at least one low oxalic acid marker located in chromosome 4. The primer and probe are same as those explained in the selection step of the production method. The kit may further contain components other than the primer and probe, such as an enzyme to be used in an amplification reaction (e.g., DNA polymerase, restriction enzyme, ribonuclease H, ligase, helicase, recombinase), a fluorescent reagent, a substrate (e.g., dNTPs, etc.), and a cofactor (e.g., ATP). The kit may further contain a positive control (e.g., housekeeping genes such as GAPDH, β-actin, β2-microglobulin, HPRT1, etc.) and/or a negative control as selection criteria, as well as two or more primers for the control. The kit may contain components each of which is in an isolated form in individual containers (e.g., tubes), or two or more components pre-mixed in the same container.

EXAMPLE

The present invention is explained in detail with reference to Examples, hereinafter. Each of the following Examples is provided for the purpose of explaining the present invention in a suitable manner, and is not intended to restrict the present invention.

Example 1 and Comparative Examples 1 to 26

(Comparison with Existing Variety in Terms of Oxalic Acid Content)

In order to develop low oxalic acid *spinacia* plants, breeding was carried out using a large number of seeds of spinach lines that were collected by successive breeding at Tohoku Kiyohara breeding station (Utsunomiya city in Tochigi prefecture). Then, an oxalic acid content was measured. As a result, a new low oxalic acid line (FERM BP-22384) with a significantly reduced content of oxalic acid was obtained.

Table 1 represents results of comparison in terms of the oxalic acid content between a deposited line (FERM BP-22384: hereinafter, simply referred to as "deposited line") with the low oxalic acid content and existing spinach varieties as control varieties (including F1 hybrid varieties sold in Japan and abroad, domestic varieties and genetic resources: Table 1) that were grown at Tohoku Kiyohara breeding station in three years, 2016, 2018, and 2019.

The investigation was conducted simultaneously when the plants were grown to approximately 20 to 30 cm in height after sowing in September and cultivating for approximately 40 days. The tips of the largest leaves were collected from five individuals in each test plot and analyzed for quantification of the oxalic acid content by the HPLC method.

TABLE 1

| | | Average oxalic acid content(mg/100 gFW) | | |
| | | Year 2016 | Year 2017 | Year 2018 |
|---|---|---|---|---|
| Example 1 | Deposited line | 490 | 281 | 462 |
| Comparative Example 1 | Surprise 7 | 1941 | 1903 | 1520 |
| Comparative Example 2 | Okame | 18 64 | | |
| Comparative Example 3 | Trad | 1833 | | |
| Comparative Example 4 | Bentenmaru | 1984 | | |
| Comparative Example 5 | Neocyclone | 1762 | | |
| Comparative Example 6 | Kite | 1843 | | |
| Comparative Example 7 | Dimple | 1503 | | |
| Comparative Example 8 | Fuyugonomi | | 2032 | |
| Comparative Example 9 | Nippon | 1613 | | |
| Comparative Example 10 | Jiromaru | 1563 | | |
| Comparative Example 11 | Nobel | 1658 | | |
| Comparative Example 12 | Whale | | 1712 | |
| Comparative Example 13 | SV2157VB | | | 1494 |
| Comparative Example 14 | Acadia | | | 12 69 |
| Comparative Example 15 | Nevada | | | 1466 |
| Comparative Example 16 | Platypus | | | 1421 |
| Comparative Example 17 | Fraja | | | 1406 |
| Comparative Example 18 | Viroflay | 2188 | 2066 | |
| Comparative Example 19 | BLOOMSDALE | 1444 | | |

TABLE 1-continued

| | | Average oxalic acid content(mg/100 gFW) | | |
| | Variety name | Year 2016 | Year 2017 | Year 2018 |
|---|---|---|---|---|
| Comparative Example 20 | USDA PI181923 | | 1965 | |
| Comparative Example 21 | USDA PI339548 | | 1965 | |
| Comparative Example 22 | USDA PI358252 | | 2030 | |
| Comparative Example 23 | USDA PI445782 | | 1910 | |
| Comparative Example 24 | USDA PI445784 | | 1793 | |
| Comparative Example 25 | USDA PI531457 | | 2011 | |
| Comparative Example 26 | USDA PI608762 | | 1682 | |

(Note in Table 1)
USDA: United States Department of Agriculture

Oxalic acid is easily accumulated in leaf tips, and all the existing spinach varieties exhibited high values (1,269 to 2,188 mg/100 g FW, 1,753 mg/100 g FW in average), whereas the deposited line exhibited consistently low values (281 to 490 mg/100 g FW) that are ⅓ to ¼ of those of the existing varieties and are remarkably low (Table 1).

Example 2 and Comparative Examples 27 and 28
(Comparison of Oxalic Acid Content in the Whole Edible Portion)

The deposited line and existing spinach varieties were grown in commercial culture media and then the oxalic acid content was measured (Table 2).

TABLE 2

| | Variety name | Average oxalic acid content (mg/100 gFW) |
|---|---|---|
| Example 2 | Deposited line | 150 |
| Comparative Example 27 | Surprise 7 | 740 |
| Comparative Example 28 | Neocyclone | 900 |

The oxalic acid content of the deposited line was as low as 150 mg/100 g FW even under soil cultivation, far below the target value. The values were ⅕ to ⅙ of those of the control varieties, and were undoubtedly lower than those of the control varieties (Table 2).

Example 3 and Comparative Examples 29 to 31
(Cultivation Characteristics)

The deposited line, mutant lines (Non-Patent Literature 10) and existing spinach varieties as control varieties (Table 3) were sown and grown outdoors at Tohoku Kiyohara breeding station (Utsunomiya city in Tochigi prefecture) on Apr. 15, 2017. The planting density was 5 cm between plants, 18 cm between rows, and 4 rows.

Harvest investigation was conducted on May 18 and 24, 2017. For the investigation, 10 individuals were harvested from each test plot and used for measurement of plant height (maximum leaf length) and weight for each plant.

Date of bolting was determined for each test plot. The date on which 15% of individuals in each test plot were bolted was defined as the date of bolting.

The results are listed in Table 3.

TABLE 3

| | | Harvest on May 18th | | Harvest on May 24th | | |
| | Variety name | Average plant height (cm) | Average weight per plant (g) | Average plant height (cm) | Average weight per plant (g) | Date of Bolting Investigation to June 4 |
|---|---|---|---|---|---|---|
| Example 3 | Deposited line | 15.8 | 14.3 | 22.6 | 28.7 | No Bolting |
| Comparative Example 29 | Mutant line (Non-Patent Literature 10) | 9.0 | 1.9 | — | — | May 19 |
| Comparative Example 30 | Neocyclone | 20.7 | 28.0 | 26.5 | 43.4 | No Bolting |
| Comparative Example 31 | Kite | 17.8 | 20.8 | 22.5 | 34.1 | No Bolting |

The investigation was conducted simultaneously when the plants were grown to approximately 20 cm in height after sowing in September 2016 and cultivating for approximately 40 days.

The analysis and determination of the oxalic acid content was requested to the Japan Food Research Laboratories and was performed by the HPLC method. Five individuals from each test plot were harvested, and the entire edible part, including the harvested leaf blade and petiole, was used for the analysis and quantification.

The deposited line was superior to the mutant lines in terms of fast growing, yield, and bolting. The deposited line was grown at the same rate or slightly slower than the control variety, but grown to sufficient height and weight with a time lag of approximately 5 days at the maximum. The bolting was not observed by June 4th until which the investigation was continued, indicating that the deposited line exhibited sufficient late bolting characteristic for spring sown crop. On the other hand, the mutant lines were bolted on May 19th, with speeds of bolting comparable to that of early-bolting domestic variety, "Nippon" (data not presented). The mutant lines were bolted, and therefore not harvested. The growth was very slow, and it is extremely difficult to cultivate.

Example 4

The F1 population was produced by hybridization between the deposited line and the spinach line with the normal oxalic acid content (Tohoku breeding line D). The individuals of the F1 population were confirmed to have normal high oxalic acid contents (1,718 to 2,015 mg/100 g FW, average 1,903 mg/100 g FW). The F2 progeny were obtained from one selfed F1 plant. Tips of largest leaves were sampled from 218 F2 individuals for the measurement of the oxalic acid content by the HPLC method.

The F2 individuals contain 59 low oxalic acid individuals with the oxalic acid content of 600 mg/100 g FW or less, and 159 high oxalic acid individuals (1,273 to 1,977 mg/100 g FW, average 1,617 mg/100 g FW). In other words, the 1:3 segregation ratio indicates that the mode of inheritance of the low oxalic acid locus of the deposited line is single recessive factor. The oxalic acid content of the deposited line studied in cultivation at the same time was 268 mg/100 g FW, and that of Tohoku breeding line D was 1,885 mg/100 g FW.

Example 5 (Low Oxalic Acid Specific SNP Marker)

The following treatments (I) and (II) were performed to identify low oxalic acid-specific SNP markers.

(I) Estimation of Causal Gene Locus Position

The oxalic acid content segregation ratio of the F2 population in Example 4 reveals that the low oxalic acid line is controlled by single recessive factor. To estimate the position, the F2 population produced in Example 4 was used for analysis using QTLseq. The sequence data obtained from the next-generation sequencer was mapped to the spinach genome sequence (LZYP01000001-LZYP01078262, 78,262 Scaffolds, obtained from NCBI) to obtain candidate SNPs. The obtained SNPs were used for marker, and further analyzed for identification of strong linkage regions to extract the scaffold codes LZYP01000033 and LZYP01001417. BLAST® search for sequences of these two Scaffolds on "SpinachBase" spinachbase.org suggested that the loci are positioned adjacent to the end of chromosome 4.

(II) Improvement of Specificity of Produced Marker

GBS (Genotyping by Sequencing) was performed to further select low oxalic acid line-specific SNPs from the SNPs obtained by QTLseq mentioned above. SNPs within Scaffold IDs LZYP01000033 and LZYP01001417 that are polymorphic among four existing spinach varieties (Tohoku breeding line D (n=6), Surprise 7 (n=10), Nippon (n=10) and Jiromaru (n=10)) and one variety of the low oxalic acid line (deposited line (n=10)), were selected. (Tables 4~6)

TABLE 4

SNP marker in Scaffold code: LZYP01000033.1 (1)

| | Marker name | | | | | | | | |
| --- | --- | --- | --- | --- | --- | --- | --- | --- | --- |
| | SL01 | SL208545 | SL220275 | SL241754 | SL293265 | SL293658 | SL293902 | SL294081 | SL430237 |
| Deposited line | A | A | A | A | A | A | A | A | A |
| Tohoku breeding line D | B | B | B | B | B | B | B | B | B |
| Surprise 7 | B | B | B | B | B | B | B | B | B |
| Nippon | B | B | B | B | B | B | B | B | B |
| Jiromaru | B | B | B | B | B | B | B | B | B |

TABLE 5

SNP marker in Scaffold code: LZYP01000033.1

| | Marker name | | | | | | | | |
| --- | --- | --- | --- | --- | --- | --- | --- | --- | --- |
| | SL747231 | SL759008 | SL812367 | SL812384 | SL812514 | SL812601 | SL1252234 | SL02 | SL2167344 |
| Deposited line | A | A | A | A | A | A | A | A | A |
| Tohoku breeding line D | B | B | B | B | B | B | B | B | B |
| Surprise 7 | B | B | B | B | B | B | B | B | B |
| Nippon | B | B | B | B | B | B | B | B | B |
| Jiromaru | B | B | B | B | B | B | B | B | B |

TABLE 6

| | SNP marker in Scaffold code: LZYP01001417.1 | | | |
| | Marker name | | | |
| | SL78812 | SL03 | SL97243 | SL323336 |
|---|---|---|---|---|
| Deposited line | A | A | A | A |
| Tohoku breeding line D | B | B | B | B |
| Surprise 7 | B | B | B | B |
| Nippon | B | B | B | B |
| Jiromaru | B | B | B | B |

(Note in Tables 4-6)

A: Low oxalic acid homozygote

B: High oxalic acid homozygote

Example 6 (Confirmation of Correlation Between Low Oxalic Acid Content *Spinacia* Plant and SNP Marker)

SNPs capable of being marked with PCR-RFLP (referred also to as CAPS (cleaved amplified polymorphic sequence)) were selected and used for marker. The PCR-RFLP protocol is as follows.

| (1) PCR reaction Reaction solution (20 μL reaction system) | |
|---|---|
| 2 × Ampdirect (registered trademark) | Plus 10 μL |
| BIOTAQTM HS DNA Polymerase | 0.1 μL |
| Primer 1 | 0.1 μL |
| Primer 2 | 0.1 μL |
| DNA sample | 1.0 μL |
| Distilled Water | 8.7 μL |

PCR Conditions

PCR was carried out at (95° C. 10 min), 35 cycles of (95° C. 30 sec)-(61° C. 30 sec)-(72° C. 1 min), followed by (72° C., 5 min).

(2) Restriction Enzyme Treatment

A restriction enzyme appropriate for each SNP marker was selected for performing restriction enzyme treatment. For example, Mbo I (Takara) was selected for the SNP at 241, 754th nucleotide of LZYP01000033.1. As a result of the restriction enzyme treatment, the polymorphic site was cleaved when the genotype was the low oxalic acid type, but not cleaved when the genotype was not the low oxalic acid type.

| Reaction solution (20 μL reaction system) | |
|---|---|
| Mbo I | 0.6 μL |
| 10 × K Buffer | 2.0 μL |
| PCR product | 5.0 μL |
| Distilled Water | 12.4 μL |

Reaction Conditions

37° C., overnight

Genotyping was performed with PCR-RFLP markers using 218 individuals from the F2 population of Example 4. Among these results, the results are listed for 16 individuals exhibiting characteristic genotypes (Table 7).

TABLE 7

| | Oxalic acid content | Marker name | | |
| Plant No. | (mg/100 gFW) | SL03 | SL01 | SL02 |
|---|---|---|---|---|
| 1 | 319 | A | A | A |
| 2 | 385 | A | A | A |
| 3 | 317 | A | A | A |
| 4 | 258 | A | A | A |
| 5 | 392 | A | A | H |
| 6 | 359 | H | A | A |
| 7 | 1613 | H | A | A |
| 8 | 1582 | H | H | A |
| 9 | 1850 | H | H | H |
| 10 | 1558 | H | H | B |
| 11 | 1422 | H | B | B |
| 12 | 1781 | B | B | H |
| 13 | 1508 | B | B | B |
| 14 | 1637 | B | B | B |
| 15 | 1751 | B | B | B |
| 16 | 1513 | B | B | B |

(Note in Table 7)

A: Low oxalic acid homozygote

B: High oxalic acid homozygote

H: Hetero

SL01 to 03 were all correlated with a low oxalic acid content. Among them, SNP (SL01) with substitution of T for the 28, 543rd A of LZYP01000033 and SNP (SL03) with substitution of A for the 90, 490th G of LZYP01001417, were found to have high correlation with the low oxalic acid content.

Example 7 (Confirmation of Specificity of PCR-RFLP Marker in Example 6)

The specificity of the PCR-RFLP marker produced in Example 6 was confirmed (n=5 for each variety). (Table 8)

TABLE 8

| | Marker name | | |
| Variety name | SL03 | SL01 | SL02 |
|---|---|---|---|
| Deposited line | A | A | A |
| Surprise 7 | B | B | B |
| Okame | B | B | B |
| Trad | B | B | B |
| Bentenmaru | B | B | B |
| Neocyclone | B | B | B |
| Kite | B | B | B |
| Dimple | B | B | B |
| Fuyugonomi | B | B | B |
| Nippon | B | B | B |
| Jiromaru | B | B | B |
| Nobel | B | B | B |
| Whale | B | B | B |
| SV2157VB | B | B | B |
| Acadia | B | B | B |
| Nevada | B | B | B |
| Platypus | B | B | B |
| Freja | B | B | B |
| Viroflay | B | B | B |
| BLOOMSDALE | B | B | B |
| USDA PI181923 | B | B | B |
| USDA PI339548 | B | B | B |
| USDA PI358252 | B | B | B |
| USDA PI445782 | B | B | B |
| USDA PI445784 | B | B | B |
| USDA PI531457 | B | B | B |
| USDA PI608762 | B | B | B |

(Note in Table 8)

A: Low oxalic acid homozygote

B: High oxalic acid homozygote

Table 8 reveals that the PCR-RFLP marker is a highly specific marker for discriminating the *spinacia* plant with the low oxalic acid content.

[Sequence Listing Free Text]

A nucleotide placed between square brackets ([ . . . ]) in the following list represents a polymorphic site.

(SEQ ID NO: 1)
SL01
5'-

CACGAAATAAGTCAAACTTATTTATTTTTCTTTTTAGTAGAAATTATCT

TTTCTAA[T]TAACTAATAATGTATATAAAAATTATCCATAAAAAATTA

CGGAG-3'

(SEQ ID NO: 2)
SL208545
5'-

AAGTTTTGATTGTTCGACATATTTTTTAAAGCGTAAAGAATTTAATGAA

A[T]AGATGTATTATGTGTTAGATATCGAAGTTGTATATGACCAAGAAG

AAAAT-3'

(SEQ ID NO: 3)
SL220275
5'-

GTTAAGGACCTCTTGCTCCTTAATCAAGGTCCCGGGTTCGAGCCTTGGA

AATGAAAAAAATCTCAACTGGGAGGATGCTGCCCATCGAAATACCCATG

CAAACTCCCGCGGAAGATTAGTCCACTCGCCGAAGG[G]CGTGGGAACT

CCTCGTAGTAGAACAAAAAAAAACAATTTGAAGAAATACTGACTATAAA

AATTTGCTGCTATTAATAAAATGTCCAATAAGTCGGTAACTATCCTTCT

TACTCCCTCCTTAAATTTGGATTGGG-3'

(SEQ ID NO: 4)
SL241754
5'-

GTCTCCCTTGAAGAGAACATAGCCAACCTCGACGAGGCCGCGACCGAGG

G[A]TCCAATAGGAGGAGTGGGTTGGTTGTTGTCTCAGCTAACTTCTGT

TTTTG-3'

(SEQ ID NO: 5)
SL293265
5'-

TGCTTATTGCAGACCGTCAATGATGTGCTTTTGGGGGTCATATCGCATG

G[T]CTATCCAAGTACGTAGGTGCCAAATCACACAAGGGTAATCAATT

CAACAA-3'

(SEQ ID NO: 6)
SL293658
5'-

AGGAAGATCAAATATGAAAGACATTTATAGAAACAG[A]AAGATAAAAA

AGGAATGGAGGGAGTAATTACTGCATAGCTGGTTGTTACGGAGTAGTTT

TCTTTTTATGCGTCAATGCCCTAATAATTGTCCTTTCTTTTTCCTTTTC

TAGCTCTGCAGCAAAGCCCTCAAGTCACTGCTATTCTGGTTGTCAATCT

ACGCGGAGTCTCTTGCTTACAGGTTGGTTGCTTATCGTTAGGTGAACAC

AAATTCACCGAAAAGGCTACATATACCCCATGGGTAT-3'

(SEQ ID NO: 7)
SL293902
5'-

AAGATAAAAAAGGAATGGAGGGAGTAATTACTGCATAGCTGGTTGTTAC

GGAGTAGTTTTCTTTTTATGCGTCAATGCCCTAATAATTGTCCTTTCTT

TTTCCTTTTCTAGCTCTGCAGCAAAGCCCTCAAGTCACTGCTATTCTGG

TTGTCAATCTACGCGGAGTCTCTTGCTTACAGGTTGGTTGCTTATCGTT

AGGTGAACACAAATTCACCGAAAAGGCTACATATACCCCATGGGTAT

[A]GAATAGTGTCATACCCTGGGCTGTGATTGGTTTAGATTTATAAATT

CCATGTGGGGTTG-3'

(SEQ ID NO: 8)
SL294081
5'-

TACTCATTGAGTATATGTATCAGCTTCCCAAATTC[G]CTGCTATTATG

GTTGTCAATATTCCATATTTTCATAGTATAAAACAAGTGTGGTATTGTA

ACAGG-3'

(SEQ ID NO: 9)
SL430237
5'-

TGAAAGTGAACCCTCCGAAATGGCATCATATTCCACCATTGAAGGAGCT

TGAGTGTTCTTCGAGGATGCGCGAGTAATAG[A]CTTAGTAAGAGCATC

CTTATTCTTATTCGGTTGTTTTCCAGAAGATTT-3'

(SEQ ID NO: 10)
SL747231
5'-

CCGTCCCTTAATACTCGACCCGTTTTGACTTTTTGCACTATTCACATAA

TTCACTTTGACCCTATTTTATTTATAGTGTATGAAAACGAATGTTAGTA

TATAATATATTGTTGGCTTCATCTTAATATATATTTTCAAAATATTAAT

ATTTTTATAAGTTTTTATAATATGTACTTAAA[A]AAATTAGTGATCAA

AGTTATGCATTAACAAACGTGTCCGATCAAAACAGATCAAGTATTAAGG

GACAGAGGGAGTACTACACGTCTACTCCAAAGTCTCAACTAGAAGCAAA

AATGGCCAACCTTAGTAGTGAAATCACGTGGAT-3'

(SEQ ID NO: 11)
SL759008
5'-

TCCTATTTTCAAAATCACACATGAAAAATGATGATGAGAAAAATCTCAC

T[G]CACTTAGTGTTTGAGGACGCTAAGACCTCATATTACCTTATTTTA

AATTA-3'

(SEQ ID NO: 12)
SL812367
5'-

TTTTCAGGAAATTGTCGATTGGAAAATTAATTTACGTCCCATTTACTCT

G[C]CAGTATCA-3'

(SEQ ID NO: 13)
SL812384
5'-

TGAACTAA[C]ATTTTATACATCTACGTGATCTACCATTATGTGTATGA

ATGTGGACCTAGGGAAGAACCTATCGGTTTTCAGTATGGCT-3'

-continued

-continued (SEQ ID NO: 14)

SL812514

5'-

TATGTTTGTGATGTCATTTGAAGTGTACAAGGTCATATTTGCTTCTTTT

T[T]AATATGTGGCACTGCACTAGATTCAATTTGTTATGAAACGAAATT

GGTCG-3'

(SEQ ID NO: 15)

SL812601

5'-

GTTT[G]GCATTTTGATTGCCAAATTGCATTTGATCAAGTGGTATACTG

GTATCTGATGTTTACCCCCGCATTGGCTATCTGATTTTATTAGTTCCCT

AATGC-3'

(SEQ ID NO: 16)

SL1252234

5'-

GAAAAATAAGATTCCAAAATTATTTTTGAATTAAAAAAGTAGGGTGCCA

CATAGATAAATAATTAGGTGTCAGATAGATATTTTATTAATTAATTACT

AATATTATGCATATACAACTTCATCAAAAAACAAGCACTCTAATAATTA

ATAATT[C]AATCTAAAATAAAATTCAATCCAAAATCAAAAATCAATCT

AATATAATATATAAAATATAGCAGTTGGTATATCTAGAAGTTTTATTTT

AACTTAACAATTTAATTAAATACGTGTATTGCACGGGCTAAAATCTAGT

ACATTATA-3'

(SEQ ID NO: 17)

SL02

5'-

AAATTGACTTT[T]AAAATCAAAGAAATGAAAACTGAATATAATACAAA

ACAAGTTGTAAGTGGATGTCTACTAACTTAGTTGGTAAGGTATTCAGGG

ATATT-3'

(SEQ ID NO: 18)

SL2167344

5'-

CCGTCCAACCCTCCGCCGGCGTCGCGTTTGAGAGAGGTAAGTTTTTCAA

AAAAAAAAATTAATTTCATTGTTGTGCCGCCCAGAAATGGCGGGTGAAG

CCATGGTTGTGCCGCCTTGGATAAGCGGTGGCGGCCATGGTTCTG[T]C

GCAGATCTTGGGTGGGTGGACCATGGCTGCCGCCGCTTATCTAGGGCGG

CACAACCATGGCTTTACACGCCATTTTTGGGCGTCAGTCAGCCA-3''

(SEQ ID NO: 19)

SL78812

5'-

TCAATCTTCACCATCTTCTCCTATTTTCCTTTAAGTTACCACACAAAGG

AAAACTAGTTTATAATTGTGTTTTCCCTTAAAAACTGTTTT[T]CATGA

AAAAT-3'

(SEQ ID NO: 20)

SL03

5'-

AGTTAGCCGCCAAGTCGATGACCTTGTCATAATATTTGTACTGGATATT

A[A]GTTTCTCAGATCTGGAGCAGTAACTAACATGGCATCCAAATGCTT

CCACT-3'

(SEQ ID NO: 21)

SL97243

5'-

AGTCGAGCTTTGACCGACTTGTGTCGAACCGGACATCGAATAATTCGCG

A[A]CAGACTCGACTCCTTAACAACCCTTAAGTACTGATATACTCTTTG

TTGGT-3'

(SEQ ID NO: 22)

SL323336

5'-

ATCAACGTTAATTATCATTAGTAAAATTATTAAACTAGTTAACCAAGGC

AACTAACAAGATGCAAAATGTACAATTGAGAAGGAGAATTCAAACATGC

AACCTATCTTACATAGATTTTAGTCTTATTTCCTCCATATTTTAAAAAA

TACGCTTTAATTAACACGTAATTTTAAAAAAAATGAGTTAAATTTATTAA

AATAATATAAAAATTGGGTAAAGGGTGAATTATTTATTA[A]-3'

---

The invention claimed is:

1. A cultivated *spinacia* plant or seed or cell thereof with a low oxalic acid content comprising at least one low oxalic acid locus located in a chromosome 4 region, wherein the *spinacia* plant or seed or cell thereof has a low oxalic acid content of 600 mg/100 g FW or less at a tip of a leaf blade, and an oxalic acid content of 400 mg/100 g FW or less at a leaf, stem or combination thereof; and wherein the low oxalic acid locus is a low oxalic acid locus possessed by the *spinacia* Deposited line, a sample deposited under Budapest Treaty with accession number: FERM BP-22384 and identified by at least one polynucleotide selected from the group consisting of the following:

a) a polynucleotide comprising the nucleotide sequence of SEQ ID NO: 1, or a nucleotide sequence comprising a mutation of at least one nucleotide other than the $57^{th}$ nucleotide in the nucleotide sequence of SEQ ID NO: 1 and that has at least 95% identity to the nucleotide sequence of SEQ ID NO: 1;

b) a polynucleotide comprising the nucleotide sequence of SEQ ID NO: 2, or a nucleotide sequence comprising a mutation of at least one nucleotide other than the 51st nucleotide in the nucleotide sequence of SEQ ID NO: 2 and that has at least 95% identity to the nucleotide sequence of SEQ ID NO: 2;

c) a polynucleotide comprising the nucleotide sequence of SEQ ID NO: 3, or a nucleotide sequence comprising a mutation of at least one nucleotide other than the $135^{th}$ nucleotide in the nucleotide sequence of SEQ ID NO: 3 and that has at least 95% identity to the nucleotide sequence of SEQ ID NO: 3;

d) a polynucleotide comprising the nucleotide sequence of SEQ ID NO: 4, or a nucleotide sequence comprising a mutation of at least one nucleotide other than the 51st nucleotide in the nucleotide sequence of SEQ ID NO: 4 and that has at least 95% identity to the nucleotide sequence of SEQ ID NO: 4;

e) a polynucleotide comprising the nucleotide sequence of SEQ ID NO: 5, or a nucleotide sequence comprising a mutation of at least one nucleotide other than the 51st nucleotide in the nucleotide sequence of SEQ ID NO: 5 and that has at least 95% identity to the nucleotide sequence of SEQ ID NO: 5;

f) a polynucleotide comprising the nucleotide sequence of SEQ ID NO: 6, or a nucleotide sequence comprising a mutation of at least one nucleotide other than the 37$^{th}$ nucleotide in the nucleotide sequence of SEQ ID NO: 6 and that has at least 95% identity to the nucleotide sequence of SEQ ID NO: 6;

g) a polynucleotide comprising the nucleotide sequence of SEQ ID NO: 7, or a nucleotide sequence comprising a mutation of at least one nucleotide other than the 244$^{th}$ nucleotide in the nucleotide sequence of SEQ ID NO: 7 and that has at least 95% identity to the nucleotide sequence of SEQ ID NO: 7;

h) a polynucleotide comprising the nucleotide sequence of SEQ ID NO: 8, or a nucleotide sequence comprising a mutation of at least one nucleotide other than the 36$^{th}$ nucleotide in the nucleotide sequence of SEQ ID NO: 8 and that has at least 95% identity to the nucleotide sequence of SEQ ID NO: 8;

i) a polynucleotide comprising the nucleotide sequence of SEQ ID NO: 9, or a nucleotide sequence comprising a mutation of at least one nucleotide other than the 81st nucleotide in the nucleotide sequence of SEQ ID NO: 9 and that has at least 95% identity to the nucleotide sequence of SEQ ID NO: 9;

j) a polynucleotide comprising the nucleotide sequence of SEQ ID NO: 10, or a nucleotide sequence comprising a mutation of at least one nucleotide other than the 180$^{th}$ nucleotide in the nucleotide sequence of SEQ ID NO: 10 and that has at least 95% identity to the nucleotide sequence of SEQ ID NO: 10;

k) a polynucleotide comprising the nucleotide sequence of SEQ ID NO: 11, or a nucleotide sequence comprising a mutation of at least one nucleotide other than the 51st nucleotide in the nucleotide sequence of SEQ ID NO: 11 and that has at least 95% identity to the nucleotide sequence of SEQ ID NO: 11;

l) a polynucleotide comprising the nucleotide sequence of SEQ ID NO: 12, or a nucleotide sequence comprising a mutation of at least one nucleotide other than the 51st nucleotide in the nucleotide sequence of SEQ ID NO: 12 and that has at least 95% identity to the nucleotide sequence of SEQ ID NO: 12;

m) a polynucleotide comprising the nucleotide sequence of SEQ ID NO: 13, or a nucleotide sequence comprising a mutation of at least one nucleotide other than the 9th nucleotide in the nucleotide sequence of SEQ ID NO: 13 and that has at least 95% identity to the nucleotide sequence of SEQ ID NO: 13;

n) a polynucleotide comprising the nucleotide sequence of SEQ ID NO: 14, or a nucleotide sequence comprising a mutation of at least one nucleotide other than the 51$^{th}$ nucleotide in the nucleotide sequence of SEQ ID NO: 14 and that has at least 95% identity to the nucleotide sequence of SEQ ID NO: 14;

o) a polynucleotide comprising the nucleotide sequence of SEQ ID NO: 15, or a nucleotide sequence comprising a mutation of at least one nucleotide other than the 5th nucleotide in the nucleotide sequence of SEQ ID NO: 15 and that has at least 95% identity to the nucleotide sequence of SEQ ID NO: 15;

p) a polynucleotide comprising the nucleotide sequence of SEQ ID NO: 16, or a nucleotide sequence comprising a mutation of at least one nucleotide other than the 154$^{th}$ nucleotide in the nucleotide sequence of SEQ ID NO: 16 and that has at least 95% identity to the nucleotide sequence of SEQ ID NO: 16;

q) a polynucleotide comprising the nucleotide sequence of SEQ ID NO: 17, or a nucleotide sequence comprising a mutation of at least one nucleotide other than the 12$^{th}$ nucleotide in the nucleotide sequence of SEQ ID NO: 17 and that has at least 95% identity to the nucleotide sequence of SEQ ID NO: 17;

r) a polynucleotide comprising the nucleotide sequence of SEQ ID NO: 18, or a nucleotide sequence comprising a mutation of at least one nucleotide other than the 144$^{th}$ nucleotide in the nucleotide sequence of SEQ ID NO: 18 and that has at least 95% identity to the nucleotide sequence of SEQ ID NO: 18;

s) a polynucleotide comprising the nucleotide sequence of SEQ ID NO: 91, or a nucleotide sequence comprising a mutation of at least one nucleotide other than the 91$^{th}$ nucleotide in the nucleotide sequence of SEQ ID NO: 19 and that has at least 95% identity to the nucleotide sequence of SEQ ID NO: 19;

t) a polynucleotide comprising the nucleotide sequence of SEQ ID NO: 20, or a nucleotide sequence comprising a mutation of at least one nucleotide other than the 51$^{th}$ nucleotide in the nucleotide sequence of SEQ ID NO: 20 and that has at least 95% identity to the nucleotide sequence of SEQ ID NO: 20;

u) a polynucleotide comprising the nucleotide sequence of SEQ ID NO: 21, or a nucleotide sequence comprising a mutation of at least one nucleotide other than the 51st nucleotide in the nucleotide sequence of SEQ ID NO: 21 and that has at least 95% identity to the nucleotide sequence of SEQ ID NO: 21; and v) a polynucleotide comprising the nucleotide sequence of SEQ ID NO: 22, or a nucleotide sequence comprising a mutation of at least one nucleotide other than the 236$^{th}$ nucleotide in the nucleotide sequence of SEQ ID NO: 22 and that has at least 95% identity to the nucleotide sequence of SEQ ID NO: 22.

2. The cultivated *spinacia* plant or seed or cell thereof according to claim 1, wherein the low oxalic acid locus is identified by at least one polynucleotide selected from the group consisting of:

a polynucleotide comprising the nucleotide sequence of SEQ ID NO: 1;

a polynucleotide comprising a mutation of at least one nucleotide other than the 57th nucleotide in the nucleotide sequence of SEQ ID NO: 1 and that has at least 95% identity to the nucleotide sequence of SEQ ID NO: 1;

a polynucleotide comprising the nucleotide sequence of SEQ ID NO: 17;

a polynucleotide comprising a mutation of at least one nucleotide other than the 12th nucleotide in the nucleotide sequence of SEQ ID NO: 17 and that has at least 95% identity to the nucleotide sequence of SEQ ID NO: 17;

a polynucleotide comprising the nucleotide sequence of SEQ ID NO: 20; and a polynucleotide comprising a mutation of at least one nucleotide other than the 51st nucleotide in the nucleotide sequence of SEQ ID NO: 20 and that has at least 95% identity to the nucleotide sequence of SEQ ID NO: 20.

3. The cultivated *spinacia* plant or seed or cell thereof according to claim 1, comprising the *spinacia* Deposited line, a sample deposited under Budapest Treaty with accession number: FERM BP-22384.

4. A method for producing a *spinacia* plant or seed or cell thereof with a low oxalic acid content, comprising cross breeding the *spinacia* plant according to claim 1 with another *spinacia* plant to produce a progeny, and selecting a progeny having at least one low oxalic acid locus in the chromosome 4 region, wherein the low oxalic acid locus is a low oxalic acid locus possessed by the *spinacia* Deposited line, the *spinacia* line deposited under Budapest Treaty with accession number: FERM BP-22384 and identified with at least one polynucleotide selected from the group consisting of the following:

a) a polynucleotide comprising the nucleotide sequence of SEQ ID NO: 1, or a nucleotide sequence comprising a mutation of at least one nucleotide other than the $57^{th}$ nucleotide in the nucleotide sequence of SEQ ID NO: 1 and that has at least 95% identity to the nucleotide sequence of SEQ ID NO: 1;

b) a polynucleotide comprising the nucleotide sequence of SEQ ID NO: 2, or a nucleotide sequence comprising a mutation of at least one nucleotide other than the 51st nucleotide in the nucleotide sequence of SEQ ID NO: 2 and that has at least 95% identity to the nucleotide sequence of SEQ ID NO: 2;

c) a polynucleotide comprising the nucleotide sequence of SEQ ID NO: 3, or a nucleotide sequence comprising a mutation of at least one nucleotide other than the $135^{th}$ nucleotide in the nucleotide sequence of SEQ ID NO: 3 and that has at least 95% identity to the nucleotide sequence of SEQ ID NO: 3;

d) a polynucleotide comprising the nucleotide sequence of SEQ ID NO: 4, or a nucleotide sequence comprising a mutation of at least one nucleotide other than the 51st nucleotide in the nucleotide sequence of SEQ ID NO: 4 and that has at least 95% identity to the nucleotide sequence of SEQ ID NO: 4;

e) a polynucleotide comprising the nucleotide sequence of SEQ ID NO: 5, or a nucleotide sequence comprising a mutation of at least one nucleotide other than the 51st nucleotide in the nucleotide sequence of SEQ ID NO: 5 and that has at least 95% identity to the nucleotide sequence of SEQ ID NO: 5;

f) a polynucleotide comprising the nucleotide sequence of SEQ ID NO: 6, or a nucleotide sequence comprising a mutation of at least one nucleotide other than the $37^{th}$ nucleotide in the nucleotide sequence of SEQ ID NO: 6 and that has at least 95% identity to the nucleotide sequence of SEQ ID NO: 6;

g) a polynucleotide comprising the nucleotide sequence of SEQ ID NO: 7, or a nucleotide sequence comprising a mutation of at least one nucleotide other than the $244^{th}$ nucleotide in the nucleotide sequence of SEQ ID NO: 7 and that has at least 95% identity to the nucleotide sequence of SEQ ID NO: 7;

h) a polynucleotide comprising the nucleotide sequence of SEQ ID NO: 8, or a nucleotide sequence comprising a mutation of at least one nucleotide other than the $36^{th}$ nucleotide in the nucleotide sequence of SEQ ID NO: 8 and that has at least 95% identity to the nucleotide sequence of SEQ ID NO: 8;

i) a polynucleotide comprising the nucleotide sequence of SEQ ID NO: 9, or a nucleotide sequence comprising a mutation of at least one nucleotide other than the 81st nucleotide in the nucleotide sequence of SEQ ID NO: 9 and that has at least 95% identity to the nucleotide sequence of SEQ ID NO: 9;

j) a polynucleotide comprising the nucleotide sequence of SEQ ID NO: 10, or a nucleotide sequence comprising a mutation of at least one nucleotide other than the $180^{th}$ nucleotide in the nucleotide sequence of SEQ ID NO: 10 and that has at least 95% identity to the nucleotide sequence of SEQ ID NO: 10;

k) a polynucleotide comprising the nucleotide sequence of SEQ ID NO: 11, or a nucleotide sequence comprising a mutation of at least one nucleotide other than the 51st nucleotide in the nucleotide sequence of SEQ ID NO: 11 and that has at least 95% identity to the nucleotide sequence of SEQ ID NO: 11;

l) a polynucleotide comprising the nucleotide sequence of SEQ ID NO: 12, or a nucleotide sequence comprising a mutation of at least one nucleotide other than the 51st nucleotide in the nucleotide sequence of SEQ ID NO: 12 and that has at least 95% identity to the nucleotide sequence of SEQ ID NO: 12;

m) a polynucleotide comprising the nucleotide sequence of SEQ ID NO: 13, or a nucleotide sequence comprising a mutation of at least one nucleotide other than the $9^{th}$ nucleotide in the nucleotide sequence of SEQ ID NO: 13 and that has at least 95% identity to the nucleotide sequence of SEQ ID NO: 13;

n) a polynucleotide comprising the nucleotide sequence of SEQ ID NO: 14, or a nucleotide sequence comprising a mutation of at least one nucleotide other than the $51^{th}$ nucleotide in the nucleotide sequence of SEQ ID NO: 14 and that has at least 95% identity to the nucleotide sequence of SEQ ID NO: 14;

o) a polynucleotide comprising the nucleotide sequence of SEQ ID NO: 15, or a nucleotide sequence comprising a mutation of at least one nucleotide other than the $5^{th}$ nucleotide in the nucleotide sequence of SEQ ID NO: 15 and that has at least 95% identity to the nucleotide sequence of SEQ ID NO: 15;

p) a polynucleotide comprising the nucleotide sequence of SEQ ID NO: 16, or a nucleotide sequence comprising a mutation of at least one nucleotide other than the $154^{th}$ nucleotide in the nucleotide sequence of SEQ ID NO: 16 and that has at least 95% identity to the nucleotide sequence of SEQ ID NO: 16;

q) a polynucleotide comprising the nucleotide sequence of SEQ ID NO: 17, or a nucleotide sequence comprising a mutation of at least one nucleotide other than the $12^{th}$ nucleotide in the nucleotide sequence of SEQ ID NO: 17 and that has at least 95% identity to the nucleotide sequence of SEQ ID NO: 17;

r) a polynucleotide comprising the nucleotide sequence of SEQ ID NO: 18, or a nucleotide sequence comprising a mutation of at least one nucleotide other than the $144^{th}$ nucleotide in the nucleotide sequence of SEQ ID NO: 18 and that has at least 95% identity to the nucleotide sequence of SEQ ID NO: 18;

s) a polynucleotide comprising the nucleotide sequence of SEQ ID NO: 91, or a nucleotide sequence comprising a mutation of at least one nucleotide other than the $91^{th}$ nucleotide in the nucleotide sequence of SEQ ID NO: 19 and that has at least 95% identity to the nucleotide sequence of SEQ ID NO: 19;

t) a polynucleotide comprising the nucleotide sequence of SEQ ID NO: 20, or a nucleotide sequence comprising a mutation of at least one nucleotide other than the $51^{th}$ nucleotide in the nucleotide sequence of SEQ ID NO: 20 and that has at least 95% identity to the nucleotide sequence of SEQ ID NO: 20;

u) a polynucleotide comprising the nucleotide sequence of SEQ ID NO: 21, or a nucleotide sequence comprising a mutation of at least one nucleotide other than the 51st nucleotide in the nucleotide sequence of SEQ ID NO:

21 and that has at least 95% identity to the nucleotide sequence of SEQ ID NO: 21; and v) a polynucleotide comprising the nucleotide sequence of SEQ ID NO: 22, or a nucleotide sequence comprising a mutation of at least one nucleotide other than the $236^{th}$ nucleotide in the nucleotide sequence of SEQ ID NO: 22 and that has at least 95% identity to the nucleotide sequence of SEQ ID NO: 22;

wherein said *spinacia* plant or seed or cell thereof with a low oxalic content fulfills at least one of an oxalic acid content of 600 mg/100 g FW or less at a tip of a leaf blade, and an oxalic acid content of 400 mg/100 g FW or less at a leaf, stem or combination thereof.

5. A method for screening *spinacia* plants or seed or cell thereof with low oxalic acid contents, wherein:

the *spinacia* plant fulfills at least one of an oxalic acid content of 600 mg/100 g FW or less at a tip of a leaf blade, and an oxalic acid content of 400 mg/100 g FW or less at a leaf, stem or combination thereof;

the method comprises selecting a cultivated *spinacia* plant having at least one low oxalic acid locus located in a chromosome 4 region; and the low oxalic acid locus is a low oxalic acid locus possessed by the *spinacia* Deposited line, a sample deposited under Budapest Treaty with accession number: FERM BP-22384 and identified with at least one polynucleotide selected from the group consisting of the following:

a) a polynucleotide comprising the nucleotide sequence of SEQ ID NO: 1, or a nucleotide sequence comprising a mutation of at least one nucleotide other than the $57^{th}$ nucleotide in the nucleotide sequence of SEQ ID NO: 1 and that has at least 95% identity to the nucleotide sequence of SEQ ID NO: 1;

b) a polynucleotide comprising the nucleotide sequence of SEQ ID NO: 2, or a nucleotide sequence comprising a mutation of at least one nucleotide other than the 51st nucleotide in the nucleotide sequence of SEQ ID NO: 2 and that has at least 95% identity to the nucleotide sequence of SEQ ID NO: 2;

c) a polynucleotide comprising the nucleotide sequence of SEQ ID NO: 3, or a nucleotide sequence comprising a mutation of at least one nucleotide other than the $135^{th}$ nucleotide in the nucleotide sequence of SEQ ID NO: 3 and that has at least 95% identity to the nucleotide sequence of SEQ ID NO: 3;

d) a polynucleotide comprising the nucleotide sequence of SEQ ID NO: 4, or a nucleotide sequence comprising a mutation of at least one nucleotide other than the 51st nucleotide in the nucleotide sequence of SEQ ID NO: 4 and that has at least 95% identity to the nucleotide sequence of SEQ ID NO: 4;

e) a polynucleotide comprising the nucleotide sequence of SEQ ID NO: 5, or a nucleotide sequence comprising a mutation of at least one nucleotide other than the 51 st nucleotide in the nucleotide sequence of SEQ ID NO: 5 and that has at least 95% identity to the nucleotide sequence of SEQ ID NO: 5;

f) a polynucleotide comprising the nucleotide sequence of SEQ ID NO: 6, or a nucleotide sequence comprising a mutation of at least one nucleotide other than the $37^{th}$ nucleotide in the nucleotide sequence of SEQ ID NO: 6 and that has at least 95% identity to the nucleotide sequence of SEQ ID NO: 6;

g) a polynucleotide comprising the nucleotide sequence of SEQ ID NO: 7, or a nucleotide sequence comprising a mutation of at least one nucleotide other than the $244^{th}$ nucleotide in the nucleotide sequence of SEQ ID NO:

7 and that has at least 95% identity to the nucleotide sequence of SEQ ID NO: 7;

h) a polynucleotide comprising the nucleotide sequence of SEQ ID NO: 8, or a nucleotide sequence comprising a mutation of at least one nucleotide other than the $36^{th}$ nucleotide in the nucleotide sequence of SEQ ID NO: 8 and that has at least 95% identity to the nucleotide sequence of SEQ ID NO: 8;

i) a polynucleotide comprising the nucleotide sequence of SEQ ID NO: 9, or a nucleotide sequence comprising a mutation of at least one nucleotide other than the 81st nucleotide in the nucleotide sequence of SEQ ID NO: 9 and that has at least 95% identity to the nucleotide sequence of SEQ ID NO: 9;

j) a polynucleotide comprising the nucleotide sequence of SEQ ID NO: 10, or a nucleotide sequence comprising a mutation of at least one nucleotide other than the $180^{th}$ nucleotide in the nucleotide sequence of SEQ ID NO: 10 and that has at least 95% identity to the nucleotide sequence of SEQ ID NO: 10;

k) a polynucleotide comprising the nucleotide sequence of SEQ ID NO: 11, or a nucleotide sequence comprising a mutation of at least one nucleotide other than the 51st nucleotide in the nucleotide sequence of SEQ ID NO: 11 and that has at least 95% identity to the nucleotide sequence of SEQ ID NO: 11;

l) a polynucleotide comprising the nucleotide sequence of SEQ ID NO: 12, or a nucleotide sequence comprising a mutation of at least one nucleotide other than the 51st nucleotide in the nucleotide sequence of SEQ ID NO: 12 and that has at least 95% identity to the nucleotide sequence of SEQ ID NO: 12;

m) a polynucleotide comprising the nucleotide sequence of SEQ ID NO: 13, or a nucleotide sequence comprising a mutation of at least one nucleotide other than the $9^{th}$ nucleotide in the nucleotide sequence of SEQ ID NO: 13 and that has at least 95% identity to the nucleotide sequence of SEQ ID NO: 13;

n) a polynucleotide comprising the nucleotide sequence of SEQ ID NO: 14, or a nucleotide sequence comprising a mutation of at least one nucleotide other than the $51^{th}$ nucleotide in the nucleotide sequence of SEQ ID NO: 14 and that has at least 95% identity to the nucleotide sequence of SEQ ID NO: 14;

o) a polynucleotide comprising the nucleotide sequence of SEQ ID NO: 15, or a nucleotide sequence comprising a mutation of at least one nucleotide other than the $5^{th}$ nucleotide in the nucleotide sequence of SEQ ID NO: 15 and that has at least 95% identity to the nucleotide sequence of SEQ ID NO: 15;

p) a polynucleotide comprising the nucleotide sequence of SEQ ID NO: 16, or a nucleotide sequence comprising a mutation of at least one nucleotide other than the $154^{th}$ nucleotide in the nucleotide sequence of SEQ ID NO: 16 and that has at least 95% identity to the nucleotide sequence of SEQ ID NO: 16;

q) a polynucleotide comprising the nucleotide sequence of SEQ ID NO: 17, or a nucleotide sequence comprising a mutation of at least one nucleotide other than the $12^{th}$ nucleotide in the nucleotide sequence of SEQ ID NO: 17 and that has at least 95% identity to the nucleotide sequence of SEQ ID NO: 17;

r) a polynucleotide comprising the nucleotide sequence of SEQ ID NO: 18, or a nucleotide sequence comprising a mutation of at least one nucleotide other than the $144^{th}$ nucleotide in the nucleotide sequence of SEQ ID NO: 18 and that has at least 95% identity to the nucleotide sequence of SEQ ID NO: 18;

s) a polynucleotide comprising the nucleotide sequence of SEQ ID NO: 91, or a nucleotide sequence comprising a mutation of at least one nucleotide other than the 91$^{th}$ nucleotide in the nucleotide sequence of SEQ ID NO: 19 and that has at least 95% identity to the nucleotide sequence of SEQ ID NO: 19;

t) a polynucleotide comprising the nucleotide sequence of SEQ ID NO: 20, or a nucleotide sequence comprising a mutation of at least one nucleotide other than the 51$^{th}$ nucleotide in the nucleotide sequence of SEQ ID NO: 20 and that has at least 95% identity to the nucleotide sequence of SEQ ID NO: 20;

u) a polynucleotide comprising the nucleotide sequence of SEQ ID NO: 21, or a nucleotide sequence comprising a mutation of at least one nucleotide other than the 51st nucleotide in the nucleotide sequence of SEQ ID NO: 21 and that has at least 95% identity to the nucleotide sequence of SEQ ID NO: 21; and v) a polynucleotide comprising the nucleotide sequence of SEQ ID NO: 22, or a nucleotide sequence comprising a mutation of at least one nucleotide other than the 236$^{th}$ nucleotide in the nucleotide sequence of SEQ ID NO: 22 and that has at least 95% identity to the nucleotide sequence of SEQ ID NO: 22.

6. A kit for screening *spinacia* plants with low oxalic acid contents, comprising at least a primer pair or a probe pair for screening *spinacia* plants with low oxalic acid, wherein:

the *spinacia* plant fulfills at least one of an oxalic acid content of 600 mg/100 g FW or less at a tip of a leaf blade, and an oxalic acid content of 400 mg/100 g FW or less at an edible portion;

wherein the primer or the probe is specifically bound to a low oxalic acid locus possessed by the *spinacia* Deposited line, a sample deposited under Budapest Treaty with accession number: FERM BP-22384 and identified with at least one polynucleotide selected from the group consisting of the following:

a) a polynucleotide comprising the nucleotide sequence of SEQ ID NO: 1, or a nucleotide sequence comprising a mutation of at least one nucleotide other than the 57$^{th}$ nucleotide in the nucleotide sequence of SEQ ID NO: 1 and that has at least 95% identity to the nucleotide sequence of SEQ ID NO: 1;

b) a polynucleotide comprising the nucleotide sequence of SEQ ID NO: 2, or a nucleotide sequence comprising a mutation of at least one nucleotide other than the 51st nucleotide in the nucleotide sequence of SEQ ID NO: 2 and that has at least 95% identity to the nucleotide sequence of SEQ ID NO: 2;

c) a polynucleotide comprising the nucleotide sequence of SEQ ID NO: 3, or a nucleotide sequence comprising a mutation of at least one nucleotide other than the 135$^{th}$ nucleotide in the nucleotide sequence of SEQ ID NO: 3 and that has at least 95% identity to the nucleotide sequence of SEQ ID NO: 3;

d) a polynucleotide comprising the nucleotide sequence of SEQ ID NO: 4, or a nucleotide sequence comprising a mutation of at least one nucleotide other than the 51st nucleotide in the nucleotide sequence of SEQ ID NO: 4 and that has at least 95% identity to the nucleotide sequence of SEQ ID NO: 4;

e) a polynucleotide comprising the nucleotide sequence of SEQ ID NO: 5, or a nucleotide sequence comprising a mutation of at least one nucleotide other than the 51st nucleotide in the nucleotide sequence of SEQ ID NO:

5 and that has at least 95% identity to the nucleotide sequence of SEQ ID NO: 5;

f) a polynucleotide comprising the nucleotide sequence of SEQ ID NO: 6, or a nucleotide sequence comprising a mutation of at least one nucleotide other than the 37$^{th}$ nucleotide in the nucleotide sequence of SEQ ID NO: 6 and that has at least 95% identity to the nucleotide sequence of SEQ ID NO: 6;

g) a polynucleotide comprising the nucleotide sequence of SEQ ID NO: 7, or a nucleotide sequence comprising a mutation of at least one nucleotide other than the 244$^{th}$ nucleotide in the nucleotide sequence of SEQ ID NO: 7 and that has at least 95% identity to the nucleotide sequence of SEQ ID NO: 7;

h) a polynucleotide comprising the nucleotide sequence of SEQ ID NO: 8, or a nucleotide sequence comprising a mutation of at least one nucleotide other than the 36$^{th}$ nucleotide in the nucleotide sequence of SEQ ID NO: 8 and that has at least 95% identity to the nucleotide sequence of SEQ ID NO: 8;

i) a polynucleotide comprising the nucleotide sequence of SEQ ID NO: 9, or a nucleotide sequence comprising a mutation of at least one nucleotide other than the 81 st nucleotide in the nucleotide sequence of SEQ ID NO: 9 and that has at least 95% identity to the nucleotide sequence of SEQ ID NO: 9;

j) a polynucleotide comprising the nucleotide sequence of SEQ ID NO: 10, or a nucleotide sequence comprising a mutation of at least one nucleotide other than the 180$^{th}$ nucleotide in the nucleotide sequence of SEQ ID NO: 10 and that has at least 95% identity to the nucleotide sequence of SEQ ID NO: 10;

k) a polynucleotide comprising the nucleotide sequence of SEQ ID NO: 11, or a nucleotide sequence comprising a mutation of at least one nucleotide other than the 51st nucleotide in the nucleotide sequence of SEQ ID NO: 11 and that has at least 95% identity to the nucleotide sequence of SEQ ID NO: 11;

l) a polynucleotide comprising the nucleotide sequence of SEQ ID NO: 12, or a nucleotide sequence comprising a mutation of at least one nucleotide other than the 51st nucleotide in the nucleotide sequence of SEQ ID NO: 12 and that has at least 95% identity to the nucleotide sequence of SEQ ID NO: 12;

m) a polynucleotide comprising the nucleotide sequence of SEQ ID NO: 13, or a nucleotide sequence comprising a mutation of at least one nucleotide other than the 9$^{th}$ nucleotide in the nucleotide sequence of SEQ ID NO: 13 and that has at least 95% identity to the nucleotide sequence of SEQ ID NO: 13;

n) a polynucleotide comprising the nucleotide sequence of SEQ ID NO: 14, or a nucleotide sequence comprising a mutation of at least one nucleotide other than the 51$^{th}$ nucleotide in the nucleotide sequence of SEQ ID NO: 14 and that has at least 95% identity to the nucleotide sequence of SEQ ID NO: 14;

o) a polynucleotide comprising the nucleotide sequence of SEQ ID NO: 15, or a nucleotide sequence comprising a mutation of at least one nucleotide other than the 5$^{th}$ nucleotide in the nucleotide sequence of SEQ ID NO: 15 and that has at least 95% identity to the nucleotide sequence of SEQ ID NO: 15;

p) a polynucleotide comprising the nucleotide sequence of SEQ ID NO: 16, or a nucleotide sequence comprising a mutation of at least one nucleotide other than the 154$^{th}$ nucleotide in the nucleotide sequence of SEQ ID NO: 16 and that has at least 95% identity to the nucleotide sequence of SEQ ID NO: 16;

q) a polynucleotide comprising the nucleotide sequence of SEQ ID NO: 17, or a nucleotide sequence comprising a mutation of at least one nucleotide other than the $12^{th}$ nucleotide in the nucleotide sequence of SEQ ID NO: 17 and that has at least 95% identity to the nucleotide sequence of SEQ ID NO: 17;

r) a polynucleotide comprising the nucleotide sequence of SEQ ID NO: 18, or a nucleotide sequence comprising a mutation of at least one nucleotide other than the $144^{th}$ nucleotide in the nucleotide sequence of SEQ ID NO: 18 and that has at least 95% identity to the nucleotide sequence of SEQ ID NO: 18;

s) a polynucleotide comprising the nucleotide sequence of SEQ ID NO: 91, or a nucleotide sequence comprising a mutation of at least one nucleotide other than the $91^{th}$ nucleotide in the nucleotide sequence of SEQ ID NO: 19 and that has at least 95% identity to the nucleotide sequence of SEQ ID NO: 19;

t) a polynucleotide comprising the nucleotide sequence of SEQ ID NO: 20, or a nucleotide sequence comprising a mutation of at least one nucleotide other than the $51^{th}$ nucleotide in the nucleotide sequence of SEQ ID NO: 20 and that has at least 95% identity to the nucleotide sequence of SEQ ID NO: 20;

u) a polynucleotide comprising the nucleotide sequence of SEQ ID NO: 21, or a nucleotide sequence comprising a mutation of at least one nucleotide other than the 51st nucleotide in the nucleotide sequence of SEQ ID NO: 21 and that has at least 95% identity to the nucleotide sequence of SEQ ID NO: 21; and v) a polynucleotide comprising the nucleotide sequence of SEQ ID NO: 22, or a nucleotide sequence comprising a mutation of at least one nucleotide other than the $236^{th}$ nucleotide in the nucleotide sequence of SEQ ID NO: 22 and that has at least 95% identity to the nucleotide sequence of SEQ ID NO: 22.

7. The method according to claim 4, wherein the low oxalic acid locus is identified by at least one polynucleotide selected from the group consisting of:

a polynucleotide comprising the nucleotide sequence of SEQ ID NO: 1;

a polynucleotide comprising a mutation of at least one nucleotide other than the 57th nucleotide in the nucleotide sequence of SEQ ID NO: 1 and that has at least 95% identity to the nucleotide sequence of SEQ ID NO: 1;

a polynucleotide comprising the nucleotide sequence of SEQ ID NO: 17;

a polynucleotide comprising a mutation of at least one nucleotide other than the 12th nucleotide in the nucleotide sequence of SEQ ID NO: 17 and that has at least 95% identity to the nucleotide sequence of SEQ ID NO: 17;

a polynucleotide comprising the nucleotide sequence of SEQ ID NO: 20; and a polynucleotide comprising a mutation of at least one nucleotide other than the 51st nucleotide in the nucleotide sequence of SEQ ID NO: 20 and that has at least 95% identity to the nucleotide sequence of SEQ ID NO: 20.

8. The method according to claim 4, wherein the *spinacia* plant or seed or cell thereof comprises a plant body or a part thereof.

9. The method according to claim 4, wherein the *spinacia* plant or seed or cell thereof comprises a seed.

10. The method plant according to claim 4, wherein the *spinacia* plant or seed or cell thereof comprises at least one selected from a plant cell, a tissue and an organ.

11. The method according to claim 5, wherein the low oxalic acid locus is identified by at least one polynucleotide selected from the group consisting of:

a polynucleotide comprising the nucleotide sequence of SEQ ID NO: 1;

a polynucleotide comprising a mutation of at least one nucleotide other than the 57th nucleotide in the nucleotide sequence of SEQ ID NO: 1 and that has at least 95% identity to the nucleotide sequence of SEQ ID NO: 1;

a polynucleotide comprising the nucleotide sequence of SEQ ID NO: 17;

a polynucleotide comprising a mutation of at least one nucleotide other than the 12th nucleotide in the nucleotide sequence of SEQ ID NO: 17 and that has at least 95% identity to the nucleotide sequence of SEQ ID NO: 17;

a polynucleotide comprising the nucleotide sequence of SEQ ID NO: 20; and a polynucleotide comprising a mutation of at least one nucleotide other than the 51st nucleotide in the nucleotide sequence of SEQ ID NO: 20 and that has at least 95% identity to the nucleotide sequence of SEQ ID NO: 20.

12. The kit according to claim 6, wherein the primer or the probe is specifically bound to at least a portion of at least one polynucleotide selected from the group consisting of:

a polynucleotide comprising the nucleotide sequence of SEQ ID NO: 1;

a polynucleotide comprising a mutation of at least one nucleotide other than the 57th nucleotide in the nucleotide sequence of SEQ ID NO: 1 and that has at least 95% identity to the nucleotide sequence of SEQ ID NO: 1;

a polynucleotide comprising the nucleotide sequence of SEQ ID NO: 17;

a polynucleotide comprising a mutation of at least one nucleotide other than the 12th nucleotide in the nucleotide sequence of SEQ ID NO: 17 and that has at least 95% identity to the nucleotide sequence of SEQ ID NO: 17;

a polynucleotide comprising the nucleotide sequence of SEQ ID NO: 20; and a polynucleotide comprising a mutation of at least one nucleotide other than the 51st nucleotide in the nucleotide sequence of SEQ ID NO: 20 and that has at least 95% identity to the nucleotide sequence of SEQ ID NO: 20.

* * * * *